United States Patent
Duggal et al.

(10) Patent No.: US 9,841,955 B2
(45) Date of Patent: Dec. 12, 2017

(54) UNIFIED OPERATING SYSTEM FOR DISTRIBUTED COMPUTING

(71) Applicant: EnterpriseWeb LLC, Glens Falls, NY (US)

(72) Inventors: Dave M. Duggal, Glens Falls, NY (US); William J. Malyk, Guelph (CA)

(73) Assignee: EnterpriseWeb LLC, Glens Falls, NY (US)

( * ) Notice: Subject to any disclaimer, the term of this patent is extended or adjusted under 35 U.S.C. 154(b) by 0 days.

(21) Appl. No.: 15/417,122

(22) Filed: Jan. 26, 2017

(65) Prior Publication Data

US 2017/0212733 A1 Jul. 27, 2017

Related U.S. Application Data

(60) Provisional application No. 62/287,201, filed on Jan. 26, 2016.

(51) Int. Cl.
*G06F 9/44* (2006.01)
*G06F 9/445* (2006.01)
(Continued)

(52) U.S. Cl.
CPC ............. *G06F 8/35* (2013.01); *G06F 8/40* (2013.01); *G06F 8/60* (2013.01); *G06F 9/44505* (2013.01);
(Continued)

(58) Field of Classification Search
CPC ..... G06F 8/34; G06F 8/35; G06F 8/40; G06F 8/60; G06F 9/44505; G06F 9/465;
(Continued)

(56) References Cited

U.S. PATENT DOCUMENTS 5,524,241 A * 6/1996 Ghoneimy ............ G06F 9/4436
  707/676
6,442,750 B1 * 8/2002 Lopes ..................... G06F 8/316
  717/126

(Continued)

OTHER PUBLICATIONS

Wegner, P., Interaction as a basis for empirical computer science, ACM Computing Surveys (CSUR) Surveys, vol. 27 Issue 1, Mar. 1995, pp. 45-48, [retrieved on Jul. 21, 2017], Retrieved from the Internet: <URL:http://dl.acm.org/>.*

(Continued)

*Primary Examiner* — Geoffrey St Leger
(74) *Attorney, Agent, or Firm* — Sheppard, Mullin, Richter & Hampton LLP

(57) ABSTRACT

In some embodiments, a real-time event is detected and context is determined based on the real-time event. An application model is fetched based on the context and meta-data associated with the real-time event, the application model referencing a micro-function and including pre-condition and post-condition descriptors. A graph is constructed based on the micro-function. The micro-function is transformed into micro-capabilities by determining a computing resource for execution of a micro-capability by matching pre-conditions and post-conditions of the micro-capability, and enabling execution and configuration of the micro-capability on the computing resource by providing access in a target environment to an API capable of calling the micro-capability to configure and execute the micro-capability. A request is received from the target environment to execute and configure the micro-capability on the computing resource. The micro-capability is executed and configured on the computing resource, and an output of the micro-capability is provided to the target environment.

21 Claims, 14 Drawing Sheets

(51) Int. Cl.
　　　*G06F 9/45*　　(2006.01)
　　　*G06F 9/46*　　(2006.01)
　　　*G06F 9/50*　　(2006.01)
　　　*G06F 9/54*　　(2006.01)

(52) U.S. Cl.
　　　CPC ............ *G06F 9/465* (2013.01); *G06F 9/5005* (2013.01); *G06F 9/5044* (2013.01); *G06F 9/5055* (2013.01); *G06F 9/54* (2013.01); *G06F 9/542* (2013.01)

(58) Field of Classification Search
　　　CPC ...... G06F 9/542; G06F 9/5005; G06F 9/5011; G06F 9/5027; G06F 9/5044; G06F 9/5055; G06F 9/54
　　　See application file for complete search history.

(56) References Cited

U.S. PATENT DOCUMENTS

| | | | |
|---|---|---|---|
| 2004/0054690 A1* | 3/2004 | Hillerbrand | G06Q 10/06 |
| 2005/0086640 A1* | 4/2005 | Kolehmainen | G06F 9/445 717/120 |
| 2008/0276064 A1 | 11/2008 | Munshi | |
| 2009/0222921 A1* | 9/2009 | Mukhopadhyay | G06N 5/04 726/23 |
| 2010/0154056 A1 | 6/2010 | Smith | |
| 2010/0199260 A1 | 8/2010 | Duggal | |
| 2011/0154374 A1* | 6/2011 | Ku | G06F 9/44505 719/320 |
| 2013/0246996 A1 | 9/2013 | Duggal | |
| 2014/0013301 A1 | 1/2014 | Duggal | |
| 2014/0075546 A1 | 3/2014 | Zeng | |
| 2014/0282448 A1* | 9/2014 | Duffy | G06F 9/45512 717/146 |
| 2015/0254309 A1* | 9/2015 | Sekiguchi | G06F 7/36 707/752 |
| 2015/0309772 A1 | 10/2015 | Duggal | |
| 2016/0062763 A1 | 3/2016 | Duggal | |
| 2016/0179482 A1* | 6/2016 | Kramer | G06F 8/34 717/107 |
| 2016/0291945 A1* | 10/2016 | Joshi | G06F 8/35 |

OTHER PUBLICATIONS

Starovic, G., et al., An Event Based Object Model for Distributed Programming, Proceedings of the 1995 International Conference on Object Oriented Information Systems, Dec. 18-20, 1995, pp. 72-86, [retrieved on Jul. 21, 2017], Retrieved from the Internet: <URL:https://link.springer.com/chapter/10.1007/978-1-4471-1009-5_7>.*

Wegner, Lutz, "A Visual Interface for Synchronous Collaboration and Negotiated Transactions," Proceedings of the Workshop on Advanced Visual Interfaces (AVI '96), pp. 156-165, May 1996.

Wegner, Peter, "Granularity of Modules in Object-Based Concurrent Systems," Proceedings of the 1988 ACM SIGPLAN Workshop on Object-Based Concurrent Programming (OOPSLA/ECOOP '88), pp. 46-49, Sep. 1988.

Wegner, Peter, "Translation Networks and Function Composition," Technical Report No. 68-10, Department of Computer Science, Cornell University, Mar. 1968.

Wegner, Peter, "Why Interaction is More Powerful than Algorithms," Communications of the ACM, vol. 40, No. 5, pp. 80-91, May 1997.

Welicki, Leon et al., "The Dynamic Factory Pattern," Proceedings of the 15th Conference on Pattern Languages of Programs (PLoP '08), Article No. 9, Oct. 2008.

Wikimedia Foundation, Inc., "Complex Adaptive System," Wikipedia online enclyclopedia entry, Jan. 14, 2016 [retrieved online at https://en.wikipedia.org/wiki/Complex_adaptive_system].

Yoder, Joseph W., "Architecture and Design of Adaptive Object-Models," ACM SIGPLAN Notices, vol. 36, No. 12, pp. 50-60, Dec. 2001.

Zhang, Lei et al., "Introducing the Omega-Machine," Proceedings of the 23rd International Conference on World Wide Web (WWW '14), pp. 905-908, Apr. 2014.

Zwicky, Fritz, "The Morphological Approach to Discovery, Invention, Research and Construction," New Methods of Thought and Procedure: Contributions to the Symposium on Methodologies, F. Zwicky and A. G. Wilson (eds.), ISBN 978-3-642-87617-2, pp. 273-297, May 1967.

International Application No. PCT/US2017/015195, International Search Report and Written Opinion dated Apr. 10, 2017.

Bojanczyk, Mikolaj et al., "Turing Machines with Atoms," In Proceedings of the 2013 28th Annual ACM/IEEE Symposium on Logic in Computer Science (LICS '13), pp. 183-192, Jun. 2013.

Braverman, Mark et al., "Towards Coding for Maximum Errors in Interactive Communication," In Proceedings of the Forty-Third Annual ACM Symposium on Theory of Computing (STOC '11), pp. 159-166, Jun. 2011.

Butler, James M., "Quantum Modeling of Distributed Object Computing," ACM SIGSIM Simulation Digest, vol. 24, No. 2, pp. 20-39, Dec. 1994.

Cardelli, Luca et al., On Understanding Types, Data Abstraction, and Polymorphism, ACM Computing Surveys (CSUR), vol. 17, No. 4, pp. 471-523, Dec. 1985.

Chargueraud, Arthur et al., "Functional Translation of a Calculus of Capabilities," In Proceedings of the 13th ACM SIGPLAN International Conference on Functional Programming (ICFP '08), pp. 213-224, Sep. 2008.

Damiani, Ferruccio, "Rank 2 Intersection Types for Local Definitions and Conditional Expressions," ACM Transactions on Programming Languages and Systems (TOPLAS), vol. 25, No. 4, pp. 401-451, Jul. 2003.

Field, John et al., "Transactors: A Programming Model for Maintaining Globally Consistent Distributed State in Unreliable Environments," Proceedings of the 32nd ACM SIGPLAN-SIGACT Symposium on Principles of Programming Languages (POPL '05), pp. 195-208, Jan. 2005.

Fuchsberger, Verena et al., "Capturing the In-Between of Interactive Artifacts and Users: A Materiality-Centered Approach," Proceedings of the 8th Nordic Conference on Human-Computer Interaction: Fun, Fast, Foundational (NordiCHI '14), pp. 451-460, Oct. 2014.

Fuchsberger, Verena et al., "Human-Computer Non-Interaction: The Activity of Non-Use," Proceedings of the 2014 Companion Publication on Designing Interactive Systems (DIS Companion '14), pp. 57-60, Jun. 2014.

Geiger, R. Stuart, "Are Computers Merely "Supporting" Cooperative Work: Towards an Ethnography of Bot Development," Proceedings of the 2013 Conference on Computer Supported Cooperative Work Companion (CSCW 13), pp. 51-56, Feb. 2013.

Geilen, Marc et al., "The Earlier the Better: A Theory of Timed Actor Interfaces," Proceedings of the 14th International Conference on Hybrid Systems: Computation and Control (HSCC '11), pp. 23-32, Apr. 2011.

Gilbert, Ira et al., "A Simple Hardware Model of a Turing Machine: Its Educational Use," Proceedings of the ACM Annual Conference, vol. 1, pp. 324-329, Aug. 1972.

Girardi, Rosario et al., "An Ontology-Based Knowledge Base for the Representation and Reuse of Software Patterns," ACM SIGSOFT Software Engineering Notes, vol. 31, No. 1, pp. 1-6, Jan. 2006.

Grosz, Barbara J., "A Multi-Agent Systems Turing Challenge," Proceedings of the 2013 International Conference on Autonomous Agents and Multi-Agent Systems (AAMAS '13), p. 3, May 2013.

Hartmanis, Juris et al., "Turing Award Lecture on Computational Complexity and the Nature of Computer Science," Communications of the ACM, vol. 37, No. 10, pp. 37-43, Oct. 1994.

Henglein, Fritz, "Type Inference with Polymorphic Recursion," ACM Transactions on Programming Languages and Systems (TOPLAS), vol. 15, No. 2, pp. 253-289, Apr. 1993.

(56) References Cited

OTHER PUBLICATIONS

Hen-Tov, Atzmon et al., "Dynamic Model Evolution," Proceedings of the 17th Conference on Pattern Languages of Programs (PLOP '10), Article No. 16, Oct. 2010.

Hewitt, Carl et al, "Actor Induction and Meta-Evaluation," Proceedings of the 1st Annual ACM SIGACT-SIGPLAN Symposium on Principles of Programming Languages (POPL '73), pp. 153-168, Oct. 1973.

Kay, Alan C., "The Early History of Smalltalk," ACM SIGPLAN Notices, vol. 28, No. 3, pp. 69-95, Mar. 1993.

Kell, Stephen, "Towards a Dynamic Object Model within Unix Processes," 2015 ACM International Symposium on New Ideas, New Paradigms, and Reflections on Programming and Software (Onward! 2015), pp. 224-239, Oct. 2015.

Kfoury, A.J. et al., "Type Reconstruction in the Presence of Polymorphic Recursion," ACM Transactions on Programming Languages and Systems (TOPLAS), vol. 15, No. 2, pp. 290-311, Apr. 1993.

Kurnia, Ilham W. et al., "A Relational Trace Logic for Simple Hierarchichal Actor-Based Component Systems," Proceedings of the 2nd Edition on Programming Systems, Languages and Applications based on Actors, Agents, and Decentralized Control Abstractions, (AGERE! 2012), pp. 47-58, Oct. 2012.

Lai, Kum-Yeq et al., "Object Lens: Letting End-Users Create Cooperative Work Applications," In Proceedings of the SIGCHI Conference on Human Factors in Computing Systems (CHI '91), pp. 425-426, Apr. 1991.

Leonard, Thomas et al., "Modelling Access Propagation in Dynamic Systems," ACM Transactions on Information and System Security (TISSEC), vol. 16, No. 2, Article No. 5, Sep. 2013.

Lesani, Mohsen et al., "Semantics-Preserving Sharing Actors," Proceedings of the 2013 Workshop on Programming based on Actors, Agents, and Cecentralized Control (AGERE! 2013), pp. 69-80, Oct. 2013.

Malone, David et al., "Modeling the 802.11 Distributed Coordinated Function in Nonsaturated Heterogeneous Conditions," IEEE/ACM Transactions on Networking (TON), vol. 15, No. 1, pp. 159-172, Feb. 2007.

Malone, David, "The Root of the Matter: Hints or Slaves," Proceedings of the 4th ACM SIGCOMM Conference on Internet Measurement (IMC '04), pp. 15-20, Oct. 2004.

Malone, Thomas W. et al, "Semistructured Messages are Surprisingly Useful for Computer-Supported Coordination," ACM Transactions on Information Systems (TOIS), vol. 5, No. 2, pp. 115-131, Apr. 1987.

Malone, Thomas W. et al., "Electronic Markets and Electronic Hierarchies," Communications of the ACM, vol. 30, No. 6, pp. 484-497, Jun. 1987.

Malone, Thomas W. et al., "Experiments with Oval: A Radically Tailorable Tool for Cooperative Work," ACM Transactions on Information Systems (TOIS), vol. 13, No. 2, pp. 177-205, Apr. 1995.

Malone, Thomas W. et al., "The Interdisciplinary Study of Coordination," ACM Computing Surveys (CSUR), vol. 26, No. 1, pp. 87-119, Mar. 1994.

Malone, Thomas W. et al., "What is Coordination Theory and How Can It Help Design Cooperative Work Systems?," Proceedings of the 1990 ACM Conference on Computer-Supported Cooperative Work (CSCW '90), pp. 357-370, Oct. 1990.

McCarthy, John, "LISP—Notes on Its Past and Future," Proceedings of the 1980 ACM Conference on LISP and Functional Programming (LFP '80), pp. .5-viii, Aug. 1980.

McCarthy, John, "LISP: A Programming System for Symbolic Manipulations," Preprints of Papers Presented at the 14th National Meeting of the Association for Computing Machinery (ACM '59), pp. 1-4, Sep. 1959.

Moran, Stuart et al., "Bridging the Analytical Gap Between Distributed Cognition and Actor Network Theory Using a Tool for Information Trajectory Analysis," Proceedings of the 30th European Conference on Cognitive Ergonomics (ECCE '12), pp. 72-77, Aug. 2012.

Musser, David R. et al., "Structured Reasoning About Actor Systems," Proceedings of the 2013 Workshop on Programming Based on Actors, Agents, and Decentralized Control (AGERE! 2013), pp. 37-48, Oct. 2013.

Odersky, Martin, "The Scala Experiment: Can We Provide Better Language Support for Component Systems?," Conference Record of the 33rd ACM SIGPLAN-SIGACT Symposium on Principles of Programming Languages (POPL 06), pp. 166-167, Jan. 2006.

Perez-Gonzalez, Hector G. et al., "Automatically Generating Object Models from Natural Language Analysis," Companion to the 17th Annual ACM SIGPLAN Conference on Object-Oriented Programming, Systems, Languages, and Applications (OOPSLA '02), pp. 86-87, Nov. 2002.

Perez-Gonzalez, Hector G. et al., "GOOAL: An Educational Object Oriented Analysis Laboratory," Companion to the 20th Annual ACM SIGPLAN Conference on Object-Oriented Programming, Systems, Languages, and Applications (OOPSLA '05), pp. 180-181, Oct. 2005.

Randall, David P. et al., "Creating Sustainable Cyberinfrastructures," Proceedings of the 33rd Annual ACM Conference on Human Factors in Computing Systems (CHI '15), pp. 1759-1768, Apr. 2015.

Rhodes, Dustin et al., "Dynamic Detection of Object Capability Violations through Model Checking," Proceedings of the 10th ACM Symposium on Dynamic Languages (DLS '14), pp. 103-112, Oct. 2014.

Rittri, Mikael, "Dimension Inference Under Polymorphic Recursion," Proceedings of the Seventh International Conference on Functional Programming Languages and Computer Architecture (FPCA '95), pp. 147-159, Jun. 1995.

Rowlands, Bruce H., "The User as Social Actor: A Focus on Systems Development Methodology Enactment," Proceedings of the 2006 ACM Symposium on Applied Computing (SAC '06), pp. 1540-1545, Apr. 2006.

Sallenave, Olivier et al., "Lightweight Generics in Embedded Systems through Static Analysis," Proceedings of be 13th ACM SIGPLAN/SIGBED International Conference on Languages, Compilers, Tools and Theory for Embedded Systems (LCTES '12), pp. 11-20, Jun. 2012.

Schonenberg, Billy et al., "Mysterious Machines," Proceedings of the 5th ACM/IEEE International Conference on Human-Robot Interaction (HRI '10), pp. 349-350, Mar. 2010.

Shackelford, Mark R. N., "Implementation Issues for an Interactive Evolutionary Computation System," Proceedings of the 9th Annual Conference Companion on Genetic and Evolutionary Computation (GECCO '07), pp. 2933-2936, Jul. 2007.

Simon, Tyler A. et al., "Multiple Objective Scheduling of HPC Workloads through Dynamic Prioritization," Proceedings of the High Performance Computing Symposium (HPC '13), Article No. 13, Apr. 2013.

Storni, Christiano et al., "Exploring ANT in PD: Reflections and Implications for Theory and Practice," Proceedings of the 12th Participatory Design Conference: Exploratory Papers, Workshop Descriptions (PDC '12), Industry Cases—vol. 2, pp. 145-146, Aug. 2012.

Van Den Brand, Mark G. J. et al., "Term Rewriting with Traversal Functions," ACM Transactions on Software Engineering and Methodology (TOSEM), vol. 12, No. 2, p. 152-190, Apr. 2003.

* cited by examiner

UNIFIED OPERATING SYSTEM FOR DISTRIBUTED COMPUTING

REFERENCE TO RELATED APPLICATIONS

The present application claims the benefit of U.S. Provisional Patent Application Ser. No. 62/287,201, filed Jan. 26, 2016 and entitled "Unified Operating System for Distributed Computing," which is incorporated herein by reference.

Aspects of the current disclosure are related to U.S. Nonprovisional patent application Ser. No. 14/936,020, which was filed on 9 Nov. 2015, which is a continuation of U.S. Nonprovisional patent application Ser. No. 14/022,033, which was filed on 9 Sep. 2013, and which is a continuation of U.S. Nonprovisional patent application Ser. No. 12/698, 361, which was filed on 2 Feb. 2010 and issued as U.S. Pat. No. 8,533,675 (included as Appendix A hereto) on 10 Sep. 2013, and which claims the benefit of U.S. Provisional Application No. 61/149,179, filed on 2 Feb. 2009, each of which is hereby incorporated by reference.

Aspects of the current disclosure also are related to U.S. Nonprovisional patent application Ser. No. 14/791,820, which was filed on 6 Jul. 2015, and which is a continuation of U.S. Nonprovisional patent application Ser. No. 13/846, 630, which was filed on 18 Mar. 2013 and issued as U.S. Pat. No. 9,075,616 (included as Appendix B hereto) on 7 Jul. 2015, and which claims the benefit of U.S. Provisional Application No. 61/612,907, which was filed on 19 Mar. 2012, each of which is hereby incorporated by reference.

TECHNICAL FIELD

The present disclosure relates generally to operating systems, and more particularly, to a unified operating system for facilitating distributed computing.

BACKGROUND

Organizations may want to be agile so they may seize opportunities, respond to threats, and generally self-improve. The ability to adapt behavior for a current context is a fundamental optimization and survival strategy. Organizations that fail to evolve with their environment are not sustainable over time.

Advances in technology (e.g. The Web, The Cloud, and now the Internet of Things) have been transforming the environment for modern organizations. A radical reduction in the cost and latency of global collaboration is enabling new business models (e.g. Netflix; Uber; AirBnB; Skype; etc.) and disrupting incumbents. Organizations that cannot adapt to this increasingly distributed and dynamic environment risk displacement.

A challenge for many organizations is that their existing information, communication and automation systems, in and of themselves, do not support this new mode of operations. While there exist innumerable software languages and technologies that satisfy a wide variety of requirements, a significant challenge is how to flexibly and dynamically connect people, information, systems and devices for a new class of 'smart' processes.

SUMMARY

Various embodiments of the present disclosure include systems, methods, and non-transitory computer readable media configured to detect one or more real-time events and determine a context based on the one or more real-time events. An application model is fetched based on the context and meta-data associated with the one or more real-time events, the application model referencing one or more micro-functions, each micro-function being a declarative model of one or more atomic functions and including at least one pre-condition descriptor and at least one post-condition descriptor. A functional graph is constructed based on the one or more micro-functions of the application model. The one or more micro-functions are transformed into a plurality of micro-capabilities, each micro-capability of the plurality of micro-capabilities being capable of satisfying at least one pre-condition of the at least one pre-condition descriptor and at least one post-condition of the at least one post-condition descriptor, by determining at least one computing resource for execution of at least one of the plurality of micro-capabilities by matching pre-conditions of the at least one micro-capability of the plurality of micro-capabilities and matching post-conditions of the at least one micro-capability of the plurality of micro-capabilities; and enabling execution and configuration of the at least one micro-capability on the at least one computing resource by providing access in a target environment to an application program interface (API), the API capable of calling the at least one micro-capability to configure the at least one micro-capability on the at least one computing resource and execute the micro-capability on the at least one computing resource. A request is received to execute and configure the at least one micro-capability on the at least one computing resource from the target environment. The at least one micro-capability is executed and configured on the at least one computing resource, and an output of the at least one micro-capability is provided from the at least one computing resource to the target environment.

In some embodiments, the one or more real-time events include a real-time system request of the target environment. In related embodiments, the real-time system request indicates an application object in a header of the real-time system request, and the context includes an identifier indicating the application object. In related embodiments, the output of the at least one micro-capability from the at least one computing resource comprises a customized representation of the requested application object.

In some embodiments, the application model, the one or more micro-functions, the plurality of micro-capabilities, and the at least one computing resource are modeled from a root object defining base properties and capabilities.

In some embodiments, the systems, methods, and non-transitory computer readable media further comprise a plurality of computing resources, wherein the plurality of computing resources includes the at least one computing resource, the plurality of computing resources providing a virtualized pool of resources, each of the plurality of computing resources being a virtualized infrastructure, a physical infrastructure, or a software-controlled device.

In some embodiments, the plurality of computing resources are distributed across a multi-dimensional network of nodes connected by one or more links.

In some embodiments, the at least one computing resource includes one or more computing resource descriptors, the one or more computing resource descriptors including an API descriptor associated with the API. In related embodiments, the one or more computing resource descriptors comprise any of one or more local interfaces, local capabilities, local services, supporting services, and operating system kernels. In related embodiments, the one or more computing resource descriptors facilitate management of thread handling, resources, and memory spaces for the at least one computing resource much as an operating system performs for a singular virtual infrastructure unit, physical infrastructure unit, or software-controlled device.

Various embodiments of the present disclosure include systems, methods, and non-transitory computer readable media configured to provide a solution for the dynamic design, construction, deployment, use, and modification of software applications on a plurality of computing resources that operate collaboratively and in parallel.

In various embodiments, the systems and methods described herein are based on a multi-paradigmatic design, bridging Metaprogramming, Functional Programming, Object Oriented Programming and Model-Driven Engineering concepts, which results in a real-time interaction-driven system that dynamically constructs the components it needs in a dataflow pipeline of virtual functions to resolve a specific system request as a contextually optimized service.

In some embodiments, applications are declarative models of requirements for desired software behavior(s), which reference, directly or indirectly, Micro-functions. The application "intent" is realized by a Software Agent, which processes a cascade of models to render concrete behavior. The Agent resolves references for Micro-functions and executes them as a dataflow pipeline of contextualized Micro-capabilities on dynamically provisioned and configured Computing Resources on a short-lived thread Various embodiments of the present disclosure include systems, methods, and non-transitory computer readable media configured to provide a federated computer system consisting of at least two computing devices and a logical and physical fabric.

In some embodiments, a system comprises a plurality of computing resources, each of which may be a tangible embodiment (e.g., a computing device) or a virtual embodiment of a group of a plurality of computing resources. The traits of these resources may be identified and made accessible through a classification scheme, providing unified access and usage of these resources independent of their embodiment.

In some embodiments, systems, methods, and non-transitory computer readable media are configured to provide a plurality of sets of small software elements, where each element embodies a single function without side effects, utilizing the resources of the underlying system embodiment through selective usage of identified traits as required for the function's embodiment. These small software elements may constitute contextualized micro-capabilities, which may be uniquely identified, and defined by their preconditions, post-conditions, and/or an embodied algorithm.

In some embodiments, systems, methods, and non-transitory computer readable media are configured to provide a plurality of sets of models and metamodels, which describe and define the interfaces and related semantics of all components of a system described herein. A metamodel may define a declarative language for the creation of a plurality of models describing the traits of the embodiment of the computing resources. These models may describe these traits in their structural aspects and in their exhibited semantics (e.g., application program interfaces (APIs)).

In some embodiments, a metamodel also may be used to define a language for the creation of a plurality of models, each of which may define the structural aspects and semantics (e.g., APIs) of a single micro-capability. The semantics defined by the model may include the algorithm embodied by the described micro-capability. Additionally, the semantics may include the preconditions that must be satisfied before invoking any execution of the algorithm embodied by the micro-capability. Preconditions may include the structure and type of any information required as input for the algorithm embodied by the micro-capability, any specific conditions of the surrounding environment required for the execution, and/or the like. These environment conditions may include all required supporting software and traits of the computing resource hosting the micro-capability embodiment. The model may further define the post-conditions holding after completion of the execution. Post-conditions may describe the structure and type of the execution results, their meaning, the specific conditions of the surrounding environment that must be met for a transfer of execution results and control flow, and/or the like.

In some embodiments, systems, methods, and non-transitory computer readable media are configured to provide ways and means to organize micro-capabilities. Micro-capabilities may follow two principles demanded by the paradigms of Model-Driven Architecture® and Functional Programming. These principles are separation of concerns and an absence of side effects. With respect to micro-capabilities, this means that each micro-capability may implement a single, distinct and atomic algorithm. It may perform the execution of this algorithm exclusively on the basis of the prevailing preconditions at the moment of invocation and may deliver results only in the form specified by the post-conditions. Besides these results, the execution may have no further effects on the surrounding environment. The conditions may be modeled as a micro-function, an implementation-independent definition (e.g., an abstract definition), sufficient to describe and classify a plurality of equivalent micro-capability embodiments hosted on a plurality of computing resources. The cascade of models used by the system transforms the micro-function into a contextualized embodiment for each use. These embodiments of micro-capabilities may be organized in a plurality of collections, like repositories or libraries. However, the definition and classification of micro-capabilities may be singular and common for all their embodiments. This enables the classification of all micro-capabilities independent of their embodiment, and provides an ability to maintain the plurality of classifications definitions for all micro-capabilities in a common catalog structure. This catalog may afford an ability to automatically derive executable solutions from the plurality of micro-capabilities.

In some embodiments, systems, methods, and non-transitory computer readable media are configured to provide a methodology and embodiment to construct executable software applications from micro-capabilities. Applications may be modeled using a declarative modeling methodology and environment. Applications may be defined in structure and function by a declarative model. This model comprises a plurality of sets of models that describe functional elements of the application as referenced micro-functions. A platform-independent embodiment (e.g., an abstract embodiment) of the application may then be constructed by assembling a solution graph from micro-function definitions based on algorithms and pre- and post-conditions. A software agent may perform a recursive transformation and combination of contextualized micro-capabilities. The result may be a complete core application, however in a representative (e.g., abstract) form, which means there is yet no real and executable embodiment of the application, but a complete composition plan listing all required micro-capabilities and their combination. After deciding the deployment target, the agent may retrieve the micro-capability embodiments built for and compatible with the traits of the execution environment and construct the application embodiment based on the composition plan (e.g., an abstract composition plan). The composition plan may provide a real-time system by deploying and executing the software as a dataflow pipeline of contextualized Micro-capabilities on dynamically provisioned and configured Computing Resources in a short-lived thread. Or, since the composition plan is completely platform-independent, it may be pre-calculated and stored, and then reused for a plurality of deployments on a plurality of target platforms.

In some embodiments, systems, methods, and non-transitory computer readable media are configured to extend the technology presented herein into a federation over a plurality of computing resource embodiments distributed across a multi-dimensional arrangement of nodes. These nodes may represent physically separated embodiments of one or more computing resources, or may represent isolated logical computing resources within a larger hosting environment. An example for the latter would be a typical datacenter arrangement, where a plurality of virtual servers is hosted by a single physical server system. Each embodiment of a computing resource may represent an autonomous, self-contained system, connected to the plurality of surrounding computing resource embodiments by the means of a communication facility. These embodiments may expect this communication facility to provide a standardized set of peer-to-peer communication services for synchronous, asynchronous and ad-hoc messaging. The underlying technology to realize these services may vary from case to case. The plurality of interconnected computing resources allows applications to include models for Distributed Operating System concerns including, but not limited to, thread handling, resource management, memory spaces, and/or the like.

In some embodiments, a fabric of interconnected computing resources may be described as nodes, interconnected by links. Each node may host a complete embodiment of an execution environment capable of executing applications constructed from an arrangement of micro-capabilities. However, not all nodes need to have the ability to perform the construction process, or require this ability. This distinction allows the inclusion of nodes with very limited resources into the federated arrangement without losing the benefits of the model-driven automated composition of applications. The minimum abilities from such a limited, or basic node may include: (1) the presence of an execution environment that supports the execution of an application composed from micro-capabilities without relying on resources outside of that node; (2) the ability to report the traits and state of this node to other nodes; (3) the ability to receive and/or replace complete applications and/or individual micro-capabilities, communicated to that node by other nodes that are part of the fabric; (4) the ability to initialize, start, stop, reset, delete, or otherwise influence loaded applications based on communications received from other nodes in the fabric; and/or the like. In an embodiment, there must be at least one node in the fabric of nodes that has extended abilities beyond the abilities of a basic node, however, there is no upper limit on the plurality of such extended nodes.

In some embodiments, systems, methods, and non-transitory computer readable media are configured to provide a method of a rigorous structural and semantic description of APIs for all micro-functions and micro-capabilities. Based on this, an automated selection, matching and combination of micro-capabilities may be provided. This may be accomplished on the model level and therefor independent of the embodiment.

DETAILED DESCRIPTION

Figure 1:
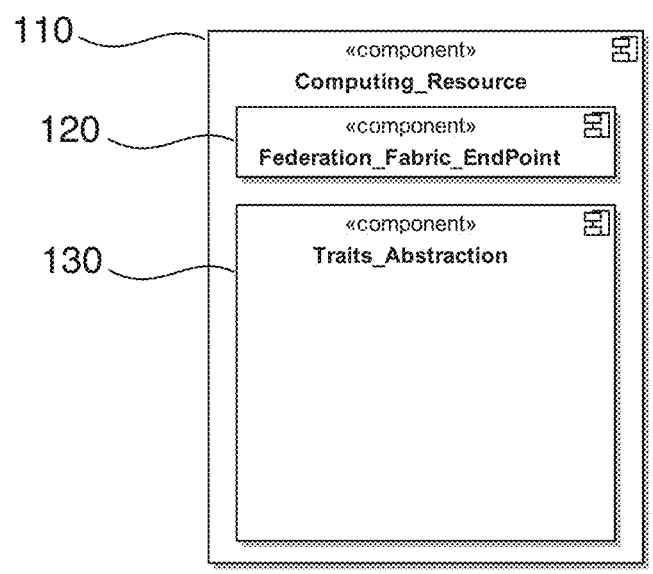
FIG. 1 shows an architecture of a computing resource according to an embodiment.

Applications are already rapidly evolving from centrally defined and controlled 'monoliths' to composite applications of Services and APIs that need to cross silos, organizational boundaries, domains, protocols and technologies. However, the prevailing application development practice is to develop software solutions on top of discrete software components required to process functional requirements (i.e. "middleware"), which results in siloed, static and brittle solutions. Middleware software components (e.g. Enterprise Service Buses; Business Process Management Suites; Complex Event Processing software; Business Rules Management Systems; API Gateways; Integration Technologies; Business Intelligence tools; etc.); are pre-integrated to form a middleware "stack". Each component generally represents a long-running synchronous process, waiting for inputs to perform transformations and output results (i.e. operations). Since all connections between applications and components, components and components, and components and their underlying infrastructure (i.e. compute, storage and network resources) are established a priori creating a tangle of fixed dependencies (i.e. "tight-coupling"), any change to this solution architecture may cause applications to fail to perform desired target behavior. In addition, this design is based on a linear series of message-passing for communicating application state between component processes with the output of one component being the input to the next component, for an ordered series of operations (i.e. "orchestration"), which ultimately results in the targeted application behavior. The middleware stack introduces its own collective overhead, which impacts development considerations regarding compute and input-output intensive applications. The linear message-passing does not lend itself to a broad real-time evaluation of application state making it more 'expensive' from a processing perspective to dynamically customize application behavior per interaction (e.g. personalize user-experience; optimize transaction; etc.). Also, since application state related to executing functions is distributed across components, if any component process (i.e. executing thread) fails, state can be lost, leading to a failed transaction with no direct compensations. As a result of these inherent limitations, the prevailing application development practice involving middleware components is a rate-limiter on emerging business requirements, business agility writ-large and the transformation of modern companies into digital businesses. accomplished through a directed and comparably slow process, constrained by the nature of the organizations and their systems. To date, exception and change management still generally remain inefficient, disconnected and largely manual processes.

Traditional engineering approaches are not necessarily capable of supporting rapid and dynamic adaptation of software systems in the dimensions of structure, functionality and spatial federation. The common practice of specifying and creating technical systems as a whole consists in the majority of cases of a single process stream, which typically leads to products forming large, cohesive units, with their characteristics "cast in stone" at a very early stage. This approach may be suitable for long-lasting infrastructure projects, like bridges or buildings, but not for information technology. However, to date, a similar single-stream process is a quite common practice in software engineering too, where it becomes more and more inappropriate, as it results in monolithic products that are difficult to maintain or change, and impossible to prove for correctness.

Many approaches have been proposed over the past decade to change this and make the development process in software engineering, or information technology in general, more agile and adaptable. A promising methodology among those is the Model-Driven Architecture® (MDA®) proposed by the Object Management Group® (OMG®). This methodology prescribes a cascade of modeling activities as the principle design phase for a system. The cascade starts with a high-level and conceptual model (e.g., abstract conceptual model), derived as a response to, and fulfillment of the system requirements. In the MDA® methodology, a sequence of model transformations follows that transition step-by-step from the conceptual model towards one or more implementable platform-specific models (PSM). During this cascade of model transformations and extensions, more and more external information is introduced to convert the concept into implementable specifications. While the pure and literal application of the MDA® methodology provides ample opportunity for change and verification along that cascade of model transformations and refinements, it still generally results in a monolithic end product. Though derived through a model-based and flexible design phase, a PSM implementation is itself a static output (i.e. the PSM is compiled to a non-portable, non-dynamic, non-adaptive, non-evolutionary platform).

Solution Overview

Changes in the way we work may require us to re-think application architecture and the middle-tier. The conventional middleware stack is being disrupted by the broader technology movements mentioned above. Successful organizations are complex adaptive systems. In some embodiments, organizational systems support a complex adaptive operation, which is capable of adapting to a changing environment through dynamic networks of interactions and individual and collective behaviors that mutate and self-organize in response to changes and events to increase an agility and sustainability of the organization.

In some embodiments, the middle-tier is a lightweight, horizontally-architected, elastically scalable layer between the end-points an organization has access to and the behavior it wants (i.e. application logic). In this manner, middleware is re-imagined as a virtualized software-defined server with a distributed operating system, which supports the composition, run-time and management of highly responsive, connected and adaptive applications with related middleware functionality realized as dynamic services, rather than discrete software components.

Re-conceptualization of the middle-tier as a virtual software-defined server with a distributed operating system may allow organizations to more naturally express themselves as complex adaptive systems.

Adaptation, as it relates to the new middle-tier may include an ability to handle each system interaction individually, as its own dynamically interpreted complex-event, in order to construct a custom policy-controlled response based on real-time operational intelligence. Instead of deploying processes that simply execute fixed models for standardized responses from static connections, a fully dynamic "situationally-aware" approach may natively support variance at the model level to personalize user-experiences, contextualize policy-enforcement, recommend or direct next-best-actions (e.g., logical workflow), and/or the like, while at the metamodel level using interaction-metadata to translate policies that drive the discovery and binding of just the relevant system objects to resolve and record the event.

An ability to support variance at the model level affords the potential for in-flight user-driven policy-constrained modifications for a single instance without disruptive exception management processes. Likewise, an ability to support variance at the metamodel level affords the potential for adaptation of any of the participating system objects, without disruptive change management processes, as the objects, or even specific versions of each object, may be found and/or bound in real-time (e.g., dynamic composition and automated interoperability for non-disruptive API evolution).

A flexible and adaptable middle-tier may be extended by queries, functions, predictive analytics machine-learning algorithms, and/or the like, which may be other endpoints that may be referenced at either the model or metamodel level.

In an embodiment, the MDA® methodology is combined with principles from Functional Programming, Functional Reactive Programming, Dataflow Programming, Metaprogramming, and the like, in a multi-paradigmatic solution. Such a combination makes a new approach explicit: instead of producing a monolithic application as specified by the PSM, build a functional equivalent application as an arrangement of lightweight functional units. These functional units may conform to functional elements found in the conceptual model or one of its early derivatives in the model cascade. Each such functional unit may implement exactly one function without further side-effects and/or conform to a common interface specification. From the perspective of Functional Decomposition, this embodiment includes, but is not limited to, functions, business entities, policies, services, applications, and/or the like, that are all described by metadata in a common pool. Interactions of this embodiment may take the form of functional chains configured by metadata as directed by models. Essentially, this may satisfy the criteria for the "Pipe-and-Filter" architectural pattern, which is also part of the REST architectural style. From a system perspective, these functional chains include, but are not limited to, system functions that perform middleware capabilities, system policies for non-functional concerns, and/or the like, that are assembled from the functional units as part of the model cascade.

Collectively, these high-level principles may be brought together in a solution that constructs the components it needs in a pipeline of virtual functions or "micro-capabilities" that exist ephemerally to resolve a specific request as a dynamically realized service. This stands in stark contrast to the current middleware stack paradigm of manually integrating purpose-built static components, and then writing static applications across them that are inherently tightly-coupled and brittle, inhibiting desired organizational agility.

Building an application as an arrangement of functional units may open up the application for change (by altering the arrangement and/or substituting functional units with alternatives), but also may provide a basis for spatial extensions. Functional units belonging to one application may be placed on alternative processing facilities, thus allowing for spatial distributed and potentially parallel execution.

While modeling is an approach to specify the desired product in various level of abstraction, meta-modeling may provide a capability to define the modeling language used to specify the product, and to specify all aspects of the production environment used to create and deploy the product, as a set of models. As a consequence, the production environment itself opens up for easy adaptation, which in turn provides yet another dimension of adaptability to the final product. Using a common approach for modeling and meta-modeling, the boundary between "design-time" and "run-time" may be allowed to vanish. Well-defined algorithms and methodologies exist to select functional units and to support construction of an arrangement representing the application.

By applying Meta-modeling concepts to MDA®, some embodiments are able to interpret models based on real-time interaction context, using a dataflow pipeline to perform transformations on-demand, resulting in declarative and dynamic solutions, this is contrast to traditional applications of MDA® for solution development where models are compiled in advance creating specific source to target transformations a priori, resulting in imperative and static programs.

In some embodiments, all elements and components of the system, including, but not limited to, Applications, Micro-functions, Micro-capabilities, Computing Resources, and the like, are modeled from a Root Object that defines base properties and capabilities (e.g. identifier, metadata descriptor, etc.). The cascade of models used to generate applications may provide a form of dataflow-based polymorphic inheritance, contextualizing all models from a common base-object, allowing the application of Object Oriented Design Patterns (e.g. Façade, Factory, etc.) to assembled Functional Programs.

Solution Components

Solution components, according to some embodiments, may be defined as follows:

Applications are declarative models of requirements for desired software behavior(s), which reference, directly or indirectly, Micro-functions. Application "intent" is realized by a Software Agent, which processes a cascade of models to render concrete behavior. An embodiment of Application is described below.

Micro-functions are declarative models of atomic functions, side-effect free and independent of implementations that are consumed by Applications. Micro-functions are explicitly modeled. Micro-functions are transformed into contextualized Micro-capabilities during execution. An embodiment of Micro-functions is described below.

Micro-capabilities are ephemeral processing intermediaries that are dynamically constructed by the Software Agent when implementing a Micro-function as a component of a solution. An embodiment of Micro-capabilities is described below Computing Resources are declarative models of infrastructure resources (i.e. virtual and tangible compute, storage and network nodes, centralized and distributed), which collectively present a hybrid distributed network as a unified pool of resources (i.e. a computational mesh, lattice, fabric, etc.). An embodiment of Computing Resources is described below.

A Software Agent is a proxy for the System, handling requests and interpreting the Declarative language in order to process the cascade of models to realize intended application behavior. Software Agents dynamically construct, alter and adapt applications in real-time, by rearranging and reconfiguring micro-capabilities based on changes in any of the models (or objects they represent). Such behavior would not be possible using traditional model-driven approached.

In some embodiments, a Software Agent is an application realized by a recursive process:
  a. Software Agent identifies "intent" by fetching an application model
  b. Constructs a corresponding functional graph based on referenced Micro-functions
  c. Transforms Micro-functions into contextualized Micro-capabilities, capable of satisfying the pre-conditions, post-conditions and functional characteristics of each Micro-function by:
     i. Determines appropriate Computing Resource for execution of the Micro-capability by matching pre-conditions, post-conditions and functional characteristics between their respective descriptors
     ii. Uses generated API descriptors for the Computing Resource to execute, deploy, connect or configure it as required by the Micro-capability
     iii. Executes the configured Micro-capability on the Computing Resource
  d. Updates the process, chaining Micro-capabilities:
     i. Using generated API descriptors to connect Micro-capabilities
  e. Recursively evaluates and chains Micro-capabilities, repeating chain until the "intent" is met.

Other Embodiments of Software Agents are described below.

Computing Resource

In some embodiments, all applications, end-user and system applications, may utilize a logically uniform computing resource to host their execution. FIG. 1 shows an architecture of a computing resource according to an embodiment. Independent from the actual embodiment, each Computing_Resource 110 may exhibit a uniform interface and a well-known set of services, divided into two categories: Local interfaces and services, represented by the Traits_Abstraction 130, and federation-related communication and remote access or invocation services provided by the Federation_Fabric_Endpoint 120. This plurality of interfaces and services may form a fixed and stable contract Computing_Resources provide, regardless of how they are embodied.

Traits are a relatively new concept, originally introduced in conjunction with the C++ meta-programming concept, but are now an intrinsic part of the latest generation of programming languages, like Scala, Swift, and others. Conceptually, traits are very similar to interfaces in that they provide a contract consisting of declarations for data structures and operations, but in contrast to regular interfaces, traits may also directly embody implementations for data structures and operations.

Computing_Resources require the incorporation of traditional operating system functionality to fulfill their service contract. The following discussion extends the architecture pattern introduced in FIG. 1 by adding an operating system component and a platform support component. Three illustrative common variations of that extended architecture pattern are discussed in conjunction with FIGS. 2A, 2B and 2C. However the plurality of variations is not limited to the shown three variants. Other variants may include, but are not limited to, nodes providing storage capabilities, networking capabilities and/or the like. To this extent, any variant fitting the pattern is implicitly included.

Figure 2A:
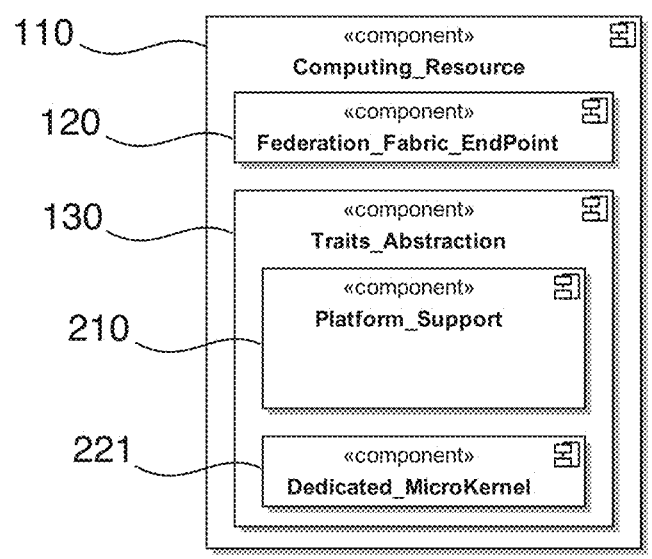
FIGS. 2A, 2B and 2C show illustrative variations of an extended architecture pattern according to embodiments.

FIG. 2A shows core operating system support required by the Computing_Resource 110 may be provided through inclusion of a Dedicated_MicroKernel 221 into the Traits_Abstraction 130. Microkernels may provide only very basic operating system services, only those requiring a privileged and protected execution environment. All other operating system services may be expected by the microkernel to be provided by processes operating in unprivileged space (often referred to as "servers"). The plurality of these services may be aggregated into the Platform_Support component 210 of the extended Computing_Resource architecture pattern.

Figure 2B:
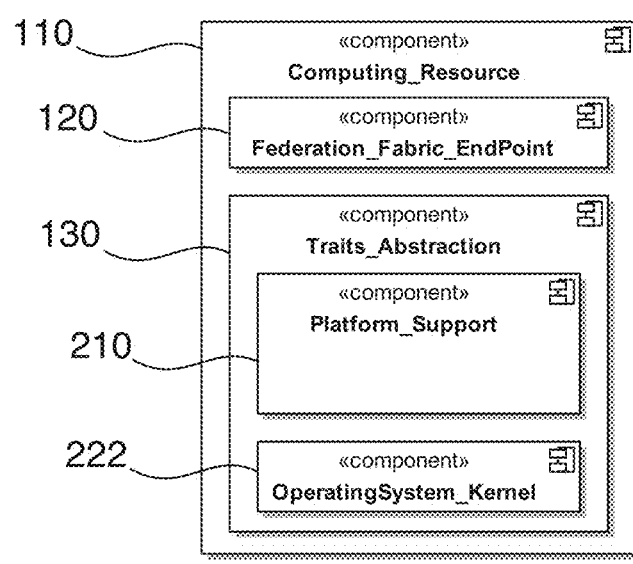

In an illustrative more "traditional" operating system environment, shown in FIG. 2B, the OperatingSystem_Kernel 222 may provide a much richer service set out of its privileged execution environment than a microkernel. As a consequence, the Platform_Support component 210 may become more lightweight.

Figure 2C:
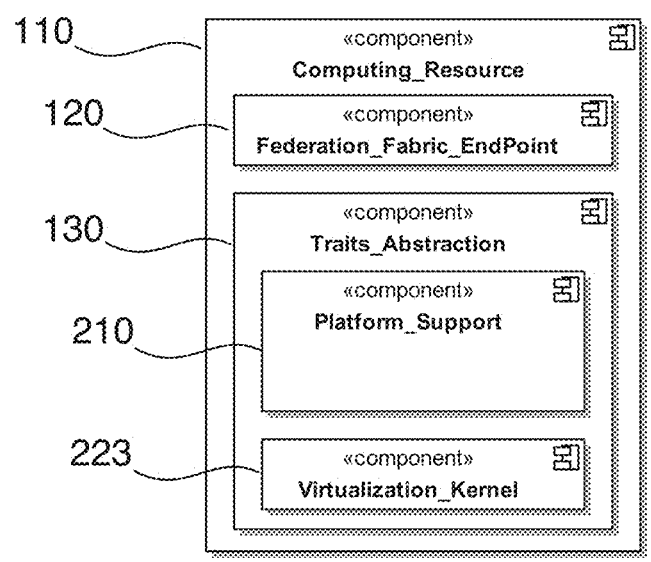

A third example variation for an extension of the basic architecture pattern, as shown in FIG. 2C, addresses virtualization. A fundamental concept of virtualization is to host a plurality of "guest" operating environments on a single "host" platform including the system's hardware and core operating system services. In this discussion, the "host" part of virtualization is not explicitly discussed and each "guest" system may be treated as an independent Computing_Resource.

In FIG. 2C, a Virtualization_Kernel 223 takes the position of the operating system component. The form and "shape" of this kernel may vary widely dependent on the virtualization technique used.

Common (in architecture terms) to the three illustrative architectural alternatives presented in FIGS. 2A, 2B and 2C is the Platform_Support component 210. An embodiment of this component may be different for any internal architecture variant of the Traits_Abstraction 130, as depicted in FIGS. 2A to 2C. The Platform_Support component 210 may provide a bridge between the provided features and interfaces of the operating system component 221, 222 and 223 and the fixed interface contract promised by the Traits_Abstraction 130.

Federation Fabric

Figure 3:
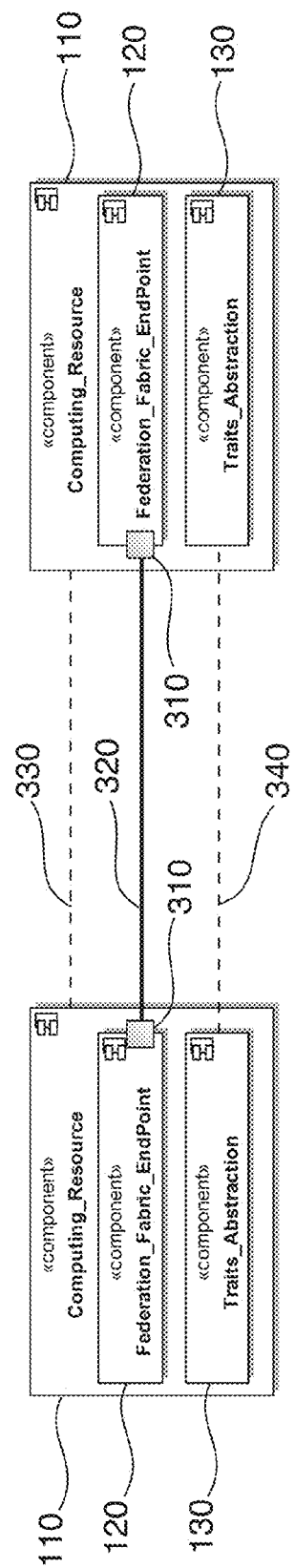
FIG. 3 shows illustrative interconnected nodes according to an embodiment.

A feature of an embodiment is the arrangement of Computing_Resources 110 as a federated and distributed computing environment. Two nodes are shown in FIG. 3 as a representation of a plurality of interconnected Computing_Resource nodes with no conceptual upper limit of the number of nodes forming this plurality. Collectively a set of interconnected Computing_Resource nodes provides a unified pool of resources (i.e. a computational mesh, lattice, fabric, etc.). This unified pool allows applications to include models for Distributed Operating System concerns including, but not limited to, thread handling, resource management, memory spaces, and/or the like.

Two nodes may be connected by means of a physical connectivity 320 between Federation_Fabric_Endpoints 120 embedded in the respective Computing_Resources 110. "Physical" in this context means any embodiment of a communication means capable of supporting a live peer-to-peer connection based on a standardized peer-to-peer communication protocol. This protocol requirement may exist only for the exhibited peer-to-peer connection; the underlying "physical" implementation may be free to use any reasonable means as long as the peer-to-peer requirements may be guaranteed and as long as embodiments of corresponding communication ports 310 compatible with both, the embodiment of the incorporating Federation_Fabric_Endpoint 120 and the characteristics of the "physical" connection scheme 320, are available.

The peer-to-peer connectivity across the communication path 320 may support the virtual direct connectivity between Computing_Resources 110 as shown as a dashed line 330 in FIG. 3, as well as a virtual direct connection between Traits_Abstractions 130, as shown by dashed line 340.

MicroCapabilities

Figure 4:
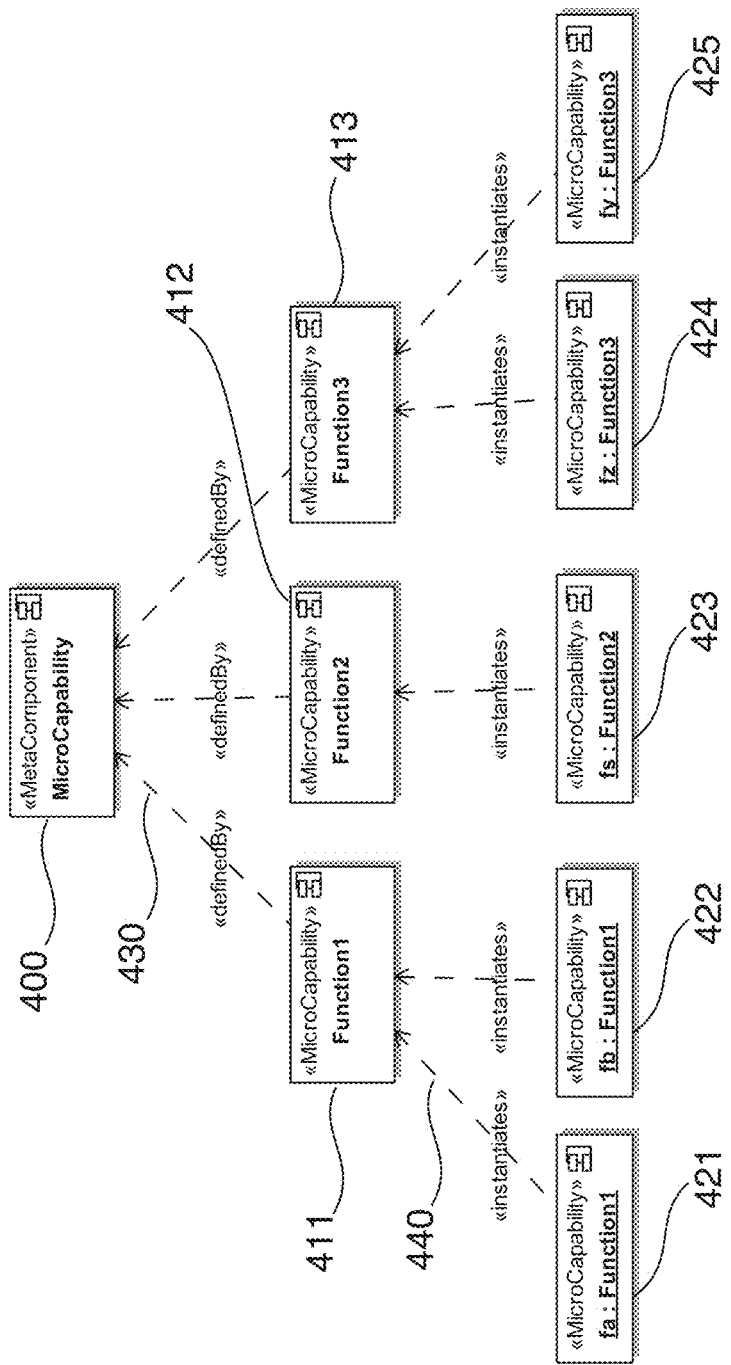
FIG. 4 shows an illustrative micro-capability meta-architecture according to an embodiment.

FIG. 4 introduces an illustrative micro-capability meta-architecture according to an embodiment. Micro-capabilities may be small functional units providing a single function without side effects. Micro-capabilities are ephemeral intermediaries for executing the function, constructed as part of the cascade of models forming a Model-driven pipeline. Applications and services may be subsequently composed by forming arrangements of micro-capabilities. This process is model-based and model-driven. FIG. 4 outlines an illustrative three-level meta-architecture for micro-capabilities.

The modeling language for all micro-capabilities may be defined by the micro-capability meta-component named MicroCapability 400, which is part of a metamodel according to an embodiment. The meta-component MicroCapability may be a logical blueprint for the modeling of a plurality of function micro-capabilities, of which three are shown as examples for the whole plurality 411, 412, 413. The fact that the meta-component MicroCapability may be a defining metamodel for those Function micro-capabilities is expressed by the dependency relationships 430, stereotyped as <<definedBy>>.

Each of the functional micro-capability (component models) may be embodied by at least one, or a plurality of, micro-capability implementations, embodying the algorithm, preconditions, and post-conditions specified in the corresponding micro-capability model. This is shown example by items 421, 422, 423, 424 and 425. An instantiation relationship is shown as dependency 440 stereotyped <<instantiates>>. Each modeled micro-capability, as for example Function1 411, may be instantiated by a plurality of sets of micro-capability instances. These sets may span a two dimensional space, where variations in the embodiment of the concrete algorithm implementing the abstract algorithm defined by the modeled micro-capability component (Function1 in this example) may represent one dimension, and the dependency of the micro-capability embodiment on the plurality of possible embodiments of the target Computing_Resource 110 may represent another dimension.

Figure 5A:
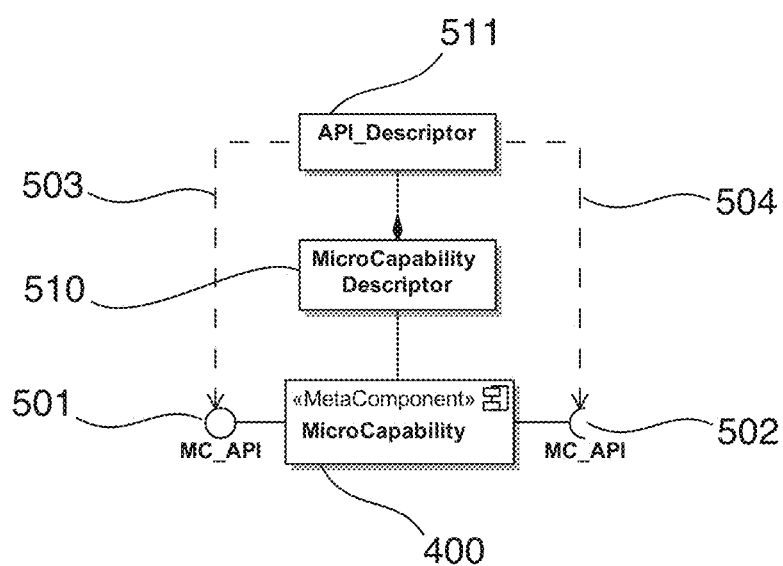
FIGS. 5A, 5B and 5C show illustrative aspects of micro-capabilities according to embodiments.

FIG. 5A shows an example expanded view of the metamodel provided by a meta-component MicroCapability 400 according to an embodiment. It shows an illustrative definition of the provided interface 501, which may expose the means and conditions to invoke the function provided by the MicroCapability; and an illustrative definition of the required interface 502 that may provide the processing results. Any receiving entity has to match this required interface in order to receive the function results correctly.

The MicroCapability Descriptor 510 may define an information model holding classification keys and formal descriptors about the functional characteristics and properties of the MicroCapability. This information may be complemented by an API_Descriptor 511, which may define the information model describing the provided and required interfaces, and all associated pre- and post-conditions. Dependency 503 may refer to the provided API 501 (and related post-conditions), while Dependency 504 may refer to the required API 502 and related post-conditions. When a micro-capability is modeled based on this metamodel, the MicroCapability Descriptor and API_Descriptor may be instantiated. Their embodiment may hold all necessary information to create, combine and deploy an embodiment of that modeled micro-capability.

Figure 5B:
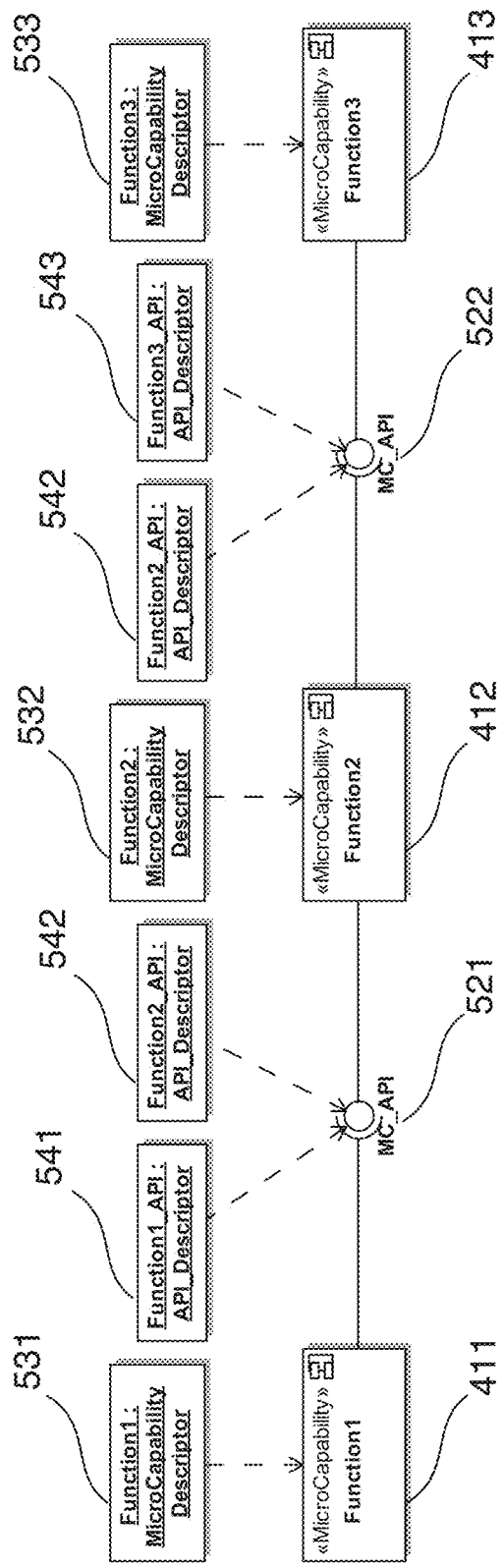

FIG. 5B shows an example arrangement of three modeled micro-capabilities, Function1 411, Function2 412 and Function3 413 according to an embodiment. These micro-capabilities may be fully described by their corresponding embodiments of MicroCapability Descriptors with names corresponding to the type name of the modeled micro-capability they describe. These are shown as 531 for Function1, 532 for Function2, and 533 for Function3. Connecting interfaces may be described by two descriptors, one for the provided interface of the downstream micro-capability and one for the required interface of the upstream micro-capability. These two interfaces may match to allow a connection. The pairing of provided and required interfaces, shown as 521, may provide the connectivity between micro-capability Function1 411 and micro-capability Function2 412. Correspondingly, embodiments of API_Descriptors may describe the details of this interface pairing 521. Part of API_Descriptor 541 may describe the required interface of micro-capability Function1 411, and part of API_Descriptor 542 may describe the matching provided interface of micro-capability Function2 412.

An equivalent arrangement may exist for the interface pairing 522 between micro-capability Function2 412 and micro-capability Function3 413, using part of API_Descriptor 542 to describe the required interface of micro-capability Function2 412, and part of API_Descriptor 543 to describe the matching provided interface of micro-capability Function3 413.

Figure 5C:
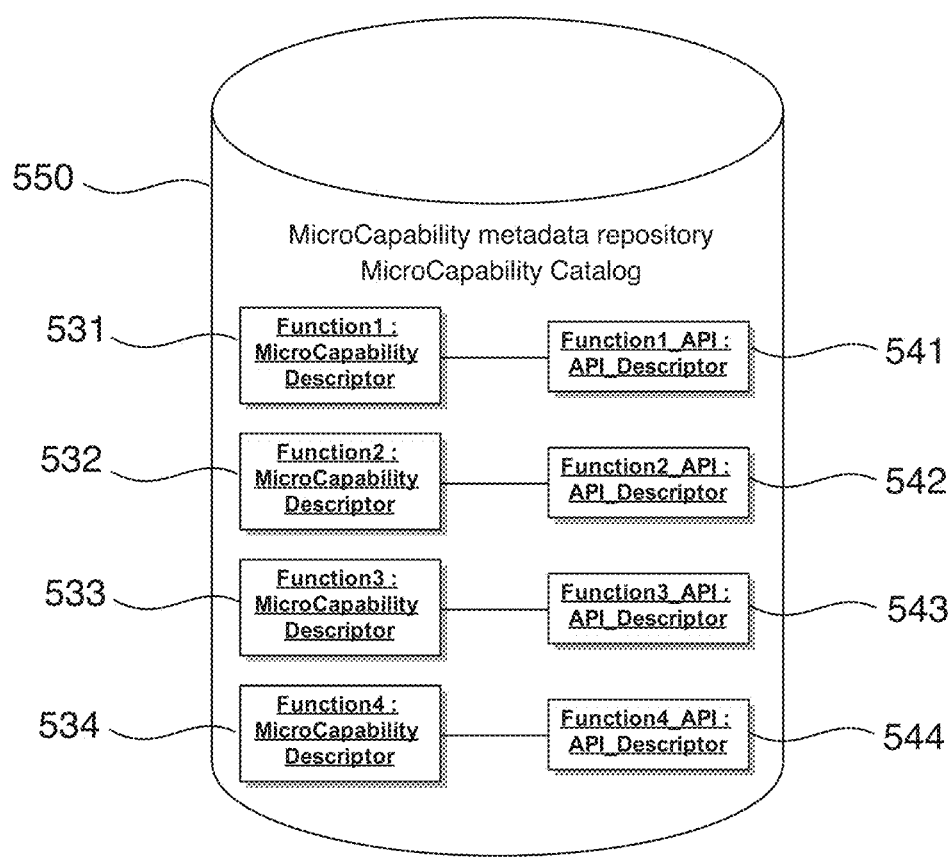

FIG. 5C shows illustrative embodiments of MicroCapability Descriptors and owned API_Descriptors, which may be stored as part of the MicroCapability metadata repository. The plurality of descriptors may comprise elements of an ontology and form a searchable catalog of platform-independent micro-capability metadata, which may be used by the Composer Agent 720 in FIG. 7 (e.g., an agent configured to perform a composer role) to construct arrangements of interface-compatible micro-capabilities, which in their totality may implement the desired application functionality.

Application Construction

Figure 6:
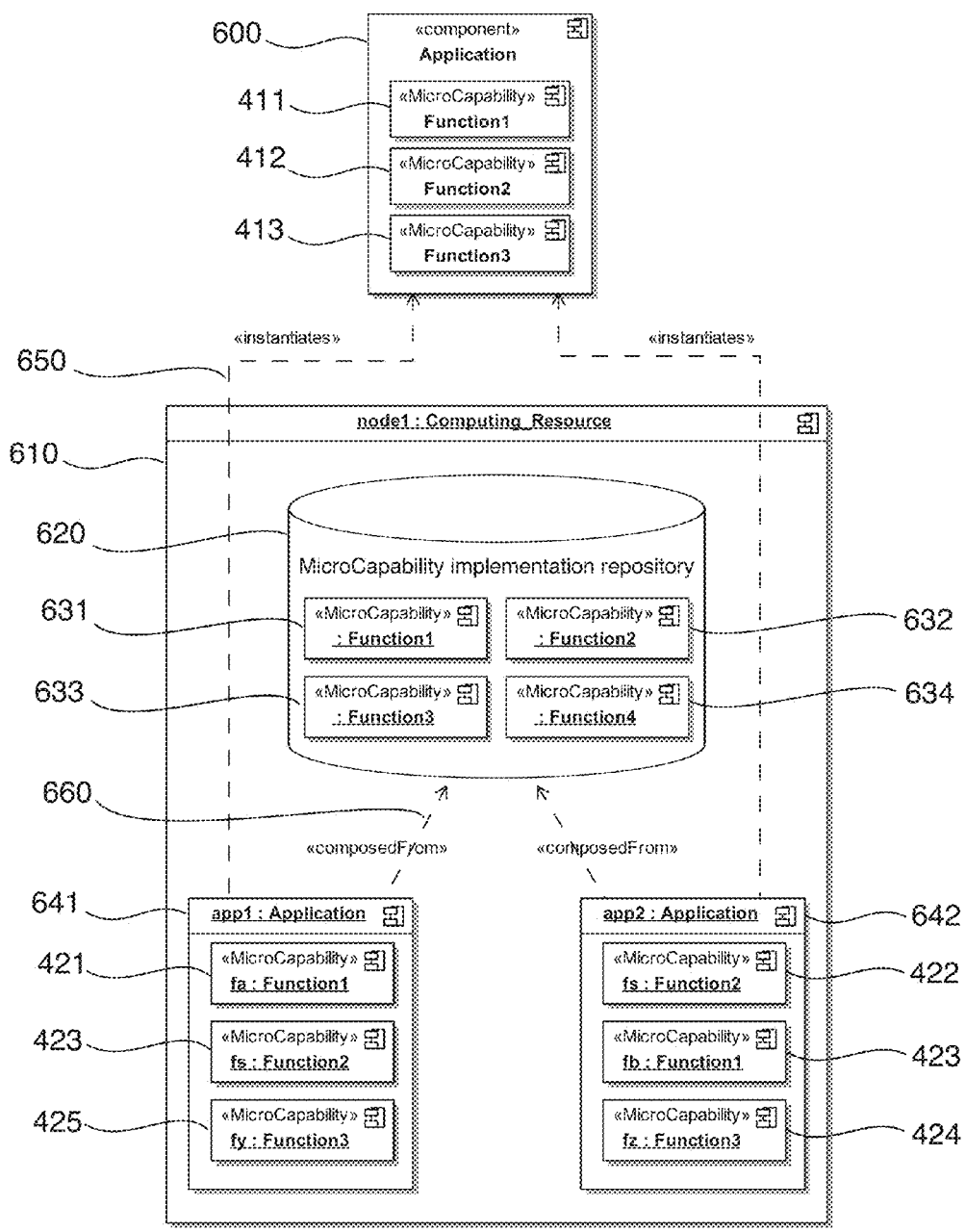
FIG. 6 shows an illustrative construction of an application model according to an embodiment.

An example construction of an Application model 600 is shown in FIG. 6 by incorporating and combining the models of three micro-capabilities, Function1 411, Function2 412 and Function3 413. Two Application embodiments, app1 641 and app2 642 may be constructed and deployed into an embodiment of a Computing_Resource named node1 610. The construction and deployment act is symbolized by the pair of dependency relationships stereotyped <<instantiates>> 650. These example embodiments of the micro-capabilities to be incorporated into the Application embodiments, following the Application model 600, may be received from the MicroCapability implementation repository 620, which can hold a set of anonymous embodiments of micro-capabilities, as shown by 631, 632, 633 and 634. Copies of these may be incorporated into the Application embodiments and named accordingly.

This example is shown by 421, 423 and 425 for app1 641, and by 422, 423 and 424 for app2 642. The fact that these Application embodiments 641, 642 may be composed from micro-capability embodiments stored in the MicroCapability implementation repository 620 is expressed by the dependency relationships stereotyped <<composedFrom>> 660.

The MicroCapability implementation repository 620 may only logically be part of the Computing_Resource embodiment node1 610. In this example, the embodiment of repository 620 may be collocated with another Computing_Resource embodiment and connected with the current Computing_Resource embodiment node1 610 by means of the peer-to-peer communication services provided by the Federation_Fabric_Endpoints 120.

Complete System Architecture

Figure 7:
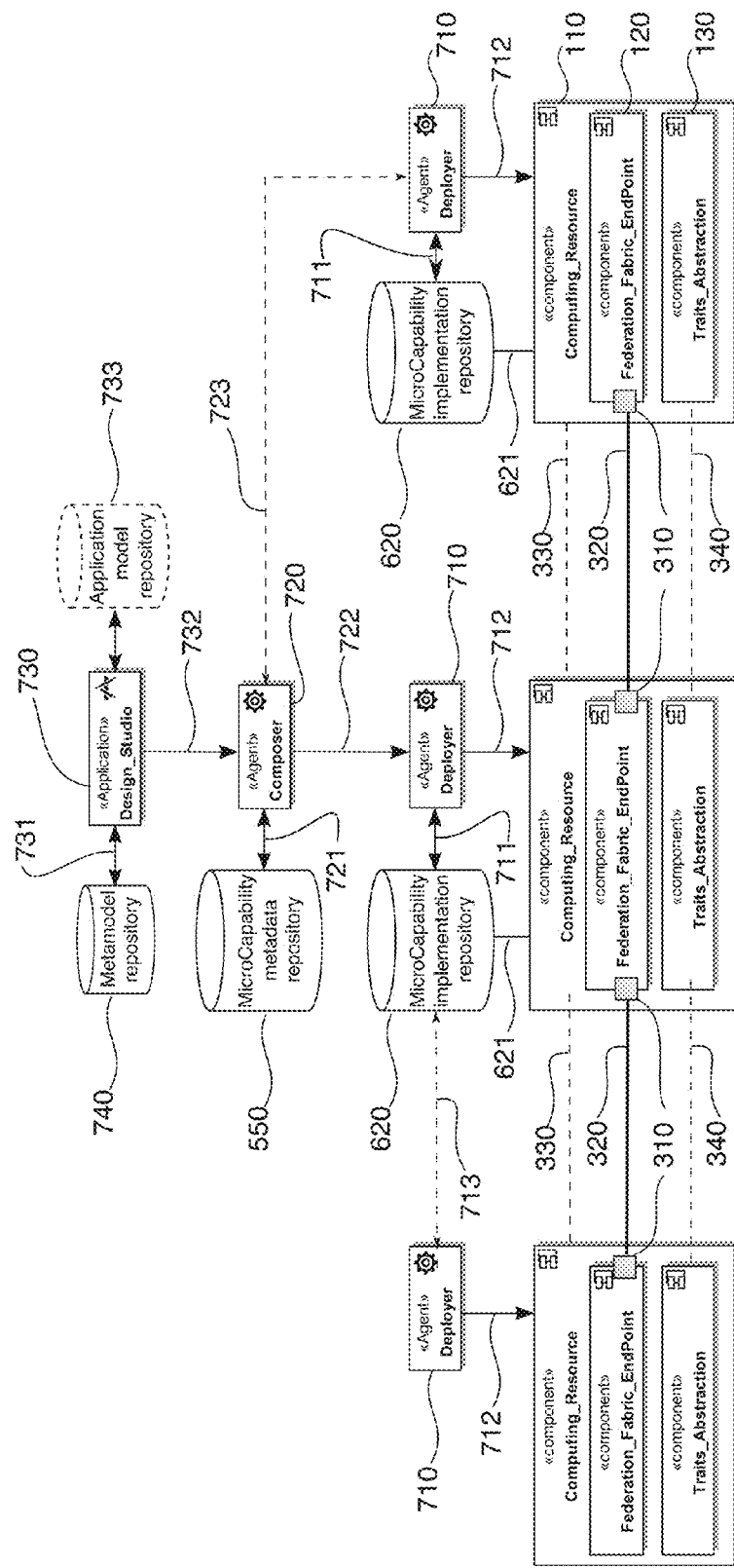
FIG. 7 shows an illustrative distributed environment according to an embodiment.

FIG. 7 shows an example distributed environment in some embodiments. FIG. 7 depicts an example chain of three Computing_Resources 110 connected by materialized communication links 320, which are linking the Federation_Fabric_Endpoints 120 through the communication ports 310 built into the Federation_Fabric_Endpoints. Virtual peer-to-peer communication between the Computing_Resources is shown as a dashed line 330. Likewise, virtual peer-to-peer communication between Traits_Abstractions is shown as dashed line 340. These virtual peer-to-peer connections can be realized by the Federation_Fabric_Endpoints over their communication link 320.

The shown three Computing_Resources may differ only in the services associated with them. They may also differ in the method of their embodiment, but on a logical level, they may be equal, as guaranteed by a provided common service contract. The Computing_Resource shown in the center of FIG. 7 may host a complete system stack, comprising the MicroCapability implementation repository 620 and the related Deployer Agent 710 (e.g., an agent configured to perform a deployer role); the MicroCapability metadata repository 550 and the related Composer Agent 720 (e.g., an agent configured to perform a composer role); and the application development environment Design_Studio 730. The Design_Studio may incorporate an embodiment of the Metamodel repository 740 that can contain all definitions of any model element used within the system. The Design_Studio 730 may have associated private application model storage 733.

In some embodiments, the Computing_Resource shown to the left in FIG. 7 may represent a minimum configuration of a node within the federated computing environment described herein. In addition to the core Computing_Resource 110, it may embody the Deployer Agent 710, which may have control over the Computing_Resource through the connection 712, but receive embodiments of micro-capability functions through the virtual connection 713 to a closely located MicroCapability implementation repository 620. In various embodiments, this connection 713 may be realized through a communication connection hosted by the Federation_Fabric_Endpoints 120 and their materialized communication link 320. In some embodiments, the peer-to-peer protocol used by the Deployer Agent 710 to the MicroCapability implementation repository 620 may follow representational state transfer (REST) principles.

The Computing_Resource shown on the right side in FIG. 7 also may host a Deployer Agent 710, as well as its private embodiment of the MicroCapability implementation repository 620. This configuration demonstrates the federation abilities of the repository architecture described herein. While repositories, the Metamodel repository 740, the MicroCapability metadata repository 550 and the MicroCapability implementation repository 620 in their totality may represent one logical repository structured with multiple meta-levels, the embodiment may use federation and replication techniques to separate implementation concerns and to improve performance of the overall system by collocating information and processing units.

Composition, configuration, and deployment of applications may be accomplished by autonomous agents on two logical levels. On the platform-independent model level, the Composer Agent 720 may accept application models from the Design_Studio 730 via the model input interface shown as the connector 732. The Composer Agent 720 (e.g., an agent configured to perform the composer role) may analyze the application model and construct an equivalent model as a lattice of interconnected micro-capabilities, using the descriptors and ontologies provided by the MicroCapability metadata repository 550 via the connector 721. An illustrative embodiment of this process is detailed in the next section. A result of this processing by the Composer Agent 720 may be a new model that includes a deployment and configuration plan. This model may be communicated to the plurality of Deployer Agents 710 (e.g., agents configured to perform the deployer role) which may construct the embodiment of the application using the appropriate combination of compatible embodiments of micro-capabilities as provided in the plurality of MicroCapability implementation repositories 620 and as directed by the deployment model communicated through connection 722 from the Composer Agent 720 to the plurality of Deployer Agents 710. The Deployer Agents 710 may be responsible to load and activate the application in the appropriate Computing_Resources 110 through their connection 712.

Application Construction Process

Figure 8:
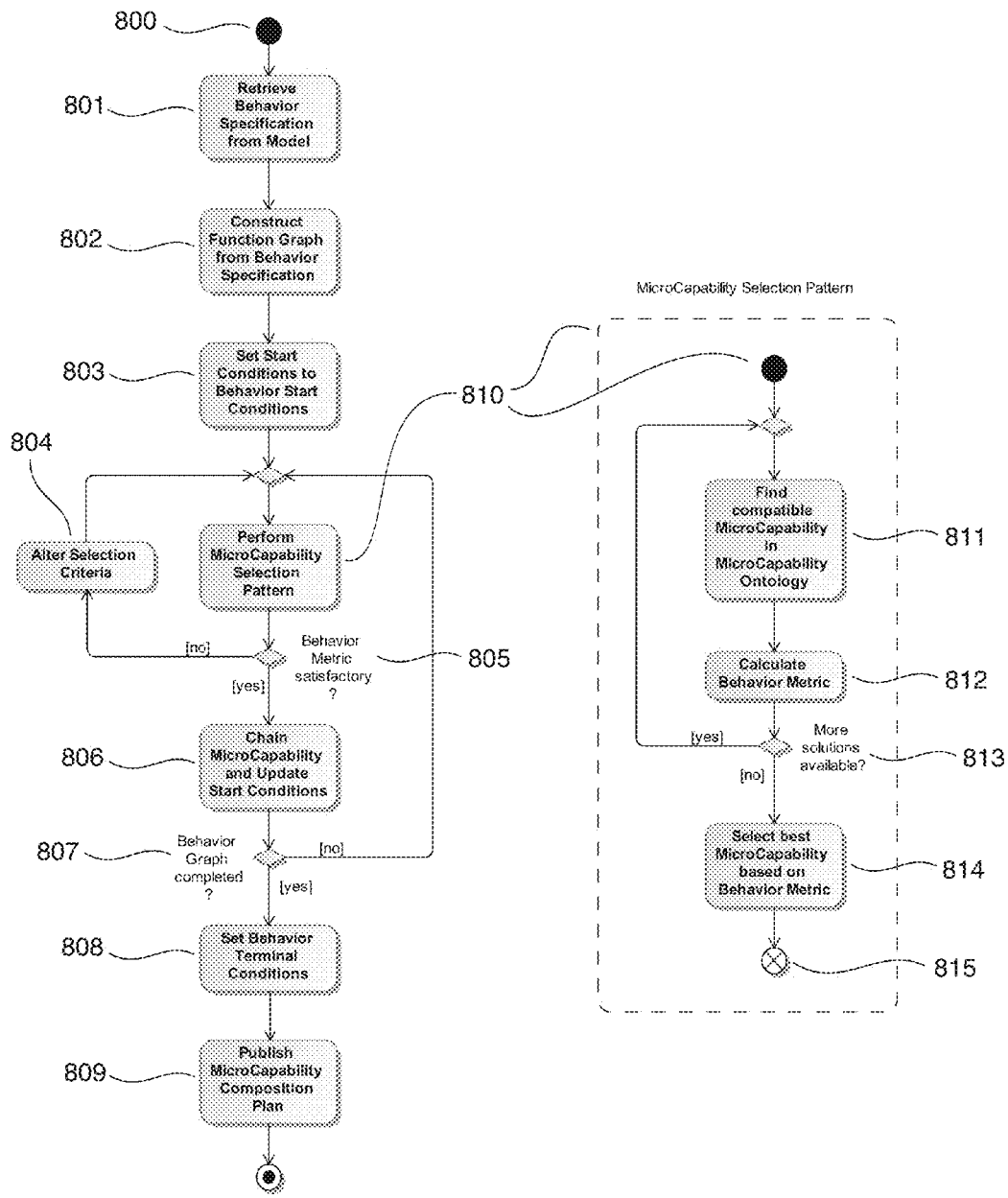
FIG. 8 shows an illustrative process for selecting and chaining micro-capabilities according to an embodiment.

FIG. 8 outlines an illustrative micro-capability selection and chaining process according to at least one embodiment. The process is entered at 800, retrieving the Behavior Specification from the application model in action 801. Action 802 derives a detailed Function Graph from the already function-oriented behavior model acquired in the previous action 801. The root of the Function Graph also may hold the Start Conditions of the application, a complex structure composed from invocation parameters, preconditions and the function's algorithm classification. In action 803, these Start Conditions are set as the seed conditions for a micro-capability search. This search may be performed as an iterative execution of the MicroCapability Selection Pattern detailed as 810. The Start Conditions may be matched against the ontology of MicroCapability Descriptors 510 and related API_Descriptors 511 in the MicroCapability metadata repository 550. This search is performed in action 811. Multiple matches are supported, which may have different quality of fulfillment of the Start Conditions but are all ontologically valid, for which the search algorithm intentionally produces a plurality of results. All results derived in action 811 can be evaluated and a qualitative metric of fulfillment (Behavior Metric) may be calculated in action 812. This search is repeated until the set of candidate micro-capabilities is determined to be exhausted in action 813. Based on the current Start Conditions, the best fitting micro-capability may be selected in action 814 and returned into the main process together with its associated Behavior Metric through the exit from the MicroCapability Selection Pattern sub-process at action 815.

The returned Behavior Metric may be evaluated against the function requirements in action 805 and the returned micro-capability can be either accepted or rejected. If it is rejected, Selection Criteria and Start Conditions may be altered and the search pattern restarted. If the returned micro-capability is accepted, then it can be chained to preceding micro-capabilities in action 806 and the Start Conditions updated. This iterative process is repeated until the whole Function Graph is satisfied. This decision is made in action 807. In action 808, the final Start conditions may be converted into Terminal Conditions, which reflect the final function results and associated post-conditions. The completed MicroCapability Composition Plan can be published for subsequent deployment through the Deployer Agents (e.g., agents configured to perform the deployer role).

Application Deployment Process

Figure 9:
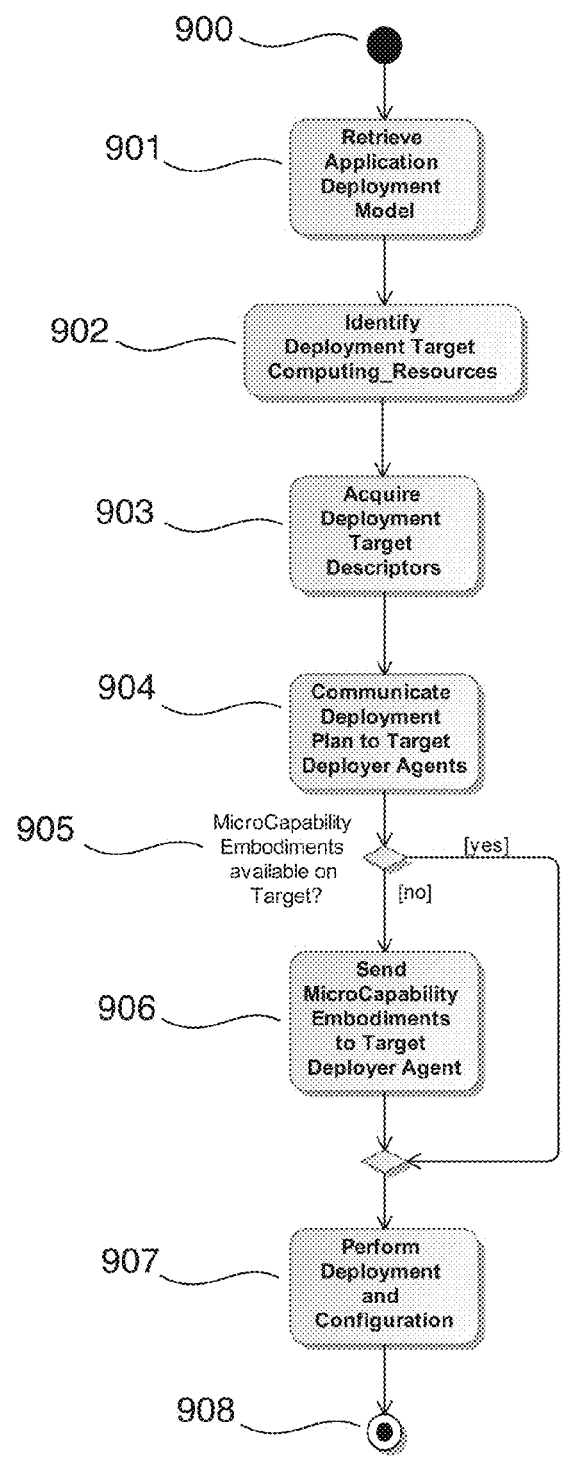
FIG. 9 shows an illustrative process of deployment and configuration of micro-capability-based applications according to an embodiment.

FIG. 9 shows an illustrative process of deployment and configuration of micro-capability-based applications according to at least one embodiment. After entering the process at 900, the Application Deployment Model may be retrieved by the Deployer Agent 710 (e.g., agent configured to perform the deployer role) in action 901. This model may include the MicroCapability Composition Plan and the model of the chained micro-capabilities as produced by the Composer Agent 720 (e.g., agent configured to perform the composer role) and described in previous section. The Deployer Agent 710 may require additional information about the set of Computing_Resource embodiments intended as deployment targets, which can be supplied in action 902. This leading Deployment Agent may contact the Deployment Agents associated with the Computing_Resource embodiments to retrieve the descriptors for each target Computing_Resource embodiments in action 903. In action 904, the leading Deployment Agent may calculate the actual Deployment Plan and communicate it to all involved target Deployment Agents. Each of the target Deployment Agents may evaluate independently if all required micro-capability embodiments (in a form compatible with the Computing_Resource embodiment) are available at the locus of the Computing_Resource embodiment 905. If this is not the case, then embodiments of all required micro-capabilities may be acquired by the target Deployment Agent through the communication facilities from the closest compatible micro-capability implementation repository 620 in action 906. This action may not be performed if all required embodiments of micro-capabilities are already present at the locus of the target Computing_Resource embodiment. Finally at action 907, the Deployer Agent associated with the target Computing_Resource embodiment performs the aggregation of micro-capability embodiments guided by the Deployment Plan and as explained herein.

This results in an executable application deployed into the target Computing_Resource embodiment at the exit action 908 of the deployment process.

Computing Environment

Figure 10:
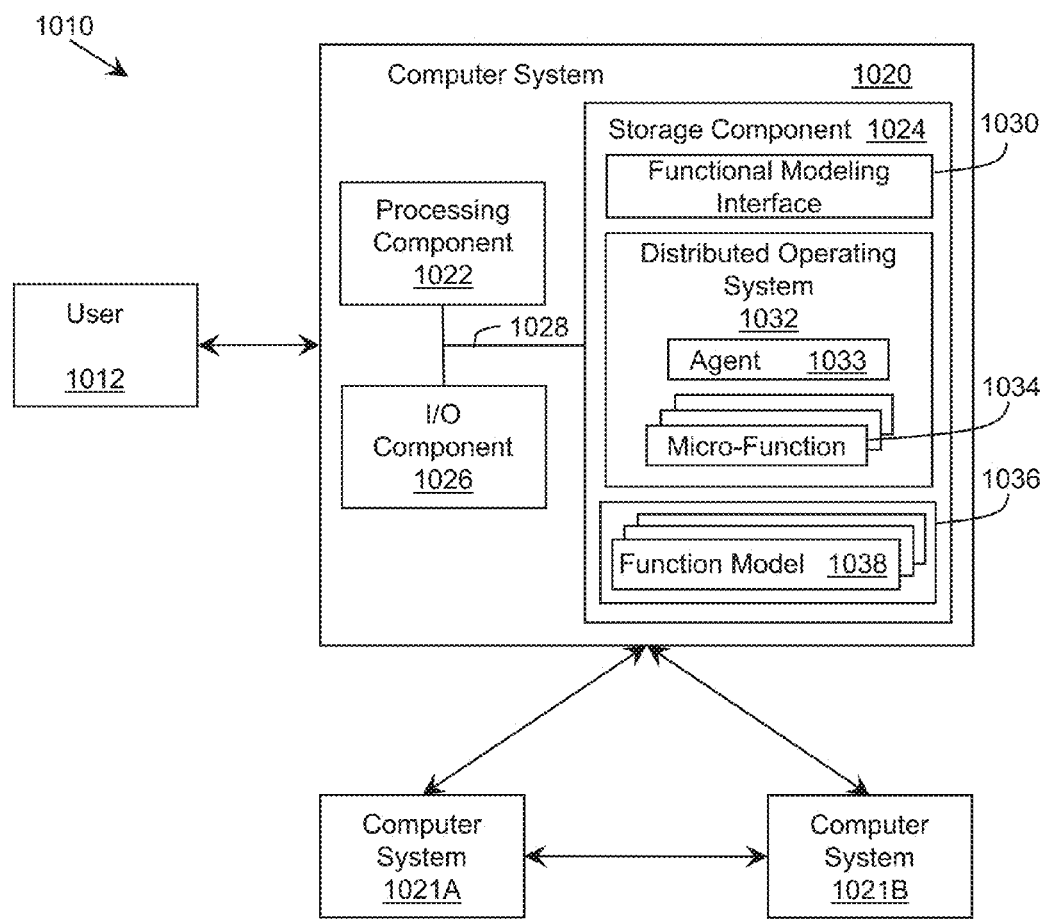
FIG. 10 shows an illustrative environment for developing a functional model-based application according to an embodiment.

FIG. 10 shows an illustrative computing environment 1010 for managing (e.g., developing, executing, and/or the like) a functional model-based application 1036 according to some embodiments. As described herein, a user 1012 (e.g., an individual, group of individuals, computing device, group of computing devices, and/or the like), may utilize a computer system 1020 (e.g., a node) of the environment 1010 to develop, configure, deploy, and/or the like, a functional model-based application 1036. To this extent, the computer system 1020 may provide a functional modeling interface 1030, which can enable the user 1012 to define, modify, and/or the like, one or more aspects of the functional model-based application 1036 using any solution. Additionally, the computer system 1020 may include a distributed operating system 1032, which may enable execution of the functional model-based application 1036 on the computer system 1020.

The computer system 1020 is shown including a processing component 1022 (e.g., one or more processors), a storage component 1024 (e.g., a storage hierarchy), an input/output (I/O) component 1026 (e.g., one or more I/O interfaces and/or devices), and a communications pathway 1028. In general, the processing component 1022 executes program code, such as a functional modeling interface 1030, which is at least partially fixed in the storage component 1024. While executing program code, the processing component 1022 may process data, which can result in reading and/or writing transformed data from/to the storage component 1024 and/or the I/O component 1026 for further processing. The pathway 1028 provides a communications link between each of the components in the computer system 1020. The I/O component 1026 may comprise one or more human I/O devices, which enable a human user 1012 to interact with the computer system 1020 and/or one or more communications devices to enable a system user 1012 to communicate with the computer system 1020 using any type of communications link. To this extent, the computer system 1020 may manage a set of interfaces (e.g., graphical user interface(s), application program interface, and/or the like) that enable human and/or system users 1012 to interact with the software executing thereon, such as the functional modeling interface 1030. Furthermore, the functional modeling interface 1030 may cause the computer system 1020 to manage (e.g., store, retrieve, create, manipulate, organize, present, or the like) the data, such as one or more functional model-based applications 1036, using any data management solution.

In any event, the computer system 1020 may comprise one or more general purpose computing articles of manufacture (e.g., computing devices) capable of executing program code installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression.

As used herein, the term "component" means any configuration of hardware, with or without software, which implements the functionality described in conjunction therewith using any solution. The term "module" means program code that enables a computer system 1020 to implement the functionality described in conjunction therewith using any solution. When fixed in a storage component 1024 of a computer system 1020 that includes a processing component 1022, a module is a substantial portion of a component that implements the functionality. Regardless, it is understood that two or more components, modules, and/or systems may share some/all of their respective hardware and/or software. Furthermore, it is understood that some of the functionality discussed herein may not be implemented or additional functionality may be included as part of the computer system 1020.

When the computer system 1020 comprises multiple computing devices, each computing device may have only a portion of a software application, such as the functional modeling interface 1030 and/or the functional model-based application 1036, fixed thereon (e.g., one or more function models 1038 of the application 1036). However, it is understood that the computer system 1020 and program code (e.g., a software application) are only representative of various possible equivalent computer systems that may perform a process described herein. To this extent, in other embodiments, the functionality provided by the computer system 1020 and program code executing thereon can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 1020 includes multiple computing devices, the computing devices may communicate over any type of communications link. Furthermore, while performing a process described herein, the computer system 1020 may communicate with one or more other computer systems using any type of communications link. In either case, the communications link may comprise any combination of various types of wired and/or wireless links; comprise any combination of one or more types of networks; and/or utilize any combination of various types of transmission techniques and protocols. In an embodiment, the computer system 1020 comprises an application server, which communicates with users 1012 over the Internet.

As discussed herein, the functional model-based application 1036 may be represented by a set of function models 1038. Each function model 1038 may define a function as a set of hardware-independent actions. A function model 1038 may reference one or more micro-functions 1034, which can be made available for use in defining the functional model-based application 1036 in a distributed operating system 1032. To this extent, the functional modeling interface 1030 may provide an interface that enables a user 1012 to define, modify, and/or the like, a function model 1038 by selecting one or more micro-functions 1034 and defining the corresponding conditions, criteria, chain, and/or the like, as described herein.

When desired, the user 1012 may deploy the functional model-based application 1036 for execution in a target computing environment 1010. As part of the deployment process, the functional model-based application 1036 may be converted into an executable application by a set of nodes, such as the computer system 1020, in the target computing environment having a distributed operating system 1032. In particular, the set of nodes in the target computing environment can comprise a distributed operating system 1032, which includes one or more agents 1033, which are configured to process the function model(s) 1038 of the application 1036. Such processing can utilize the micro-functions 1034 to convert device-independent references for the corresponding micro-functions into implementations of the micro-functions capable of performing the corresponding micro-function within the target computing environment as contextualized micro-capabilities 1010. The micro-functions 1034 may provide the functional model-based application 1036 with unified access and usage of resources independent of their embodiment. As discussed herein, such a conversion may occur in real-time during execution of the functional model-based application 1036, thereby enabling the execution of the functional model-based application 1036 to be highly responsive to changes to the target computing environment.

The computing environment 1010 may include a fabric of interconnected computing resources, which includes computer system 1020 as well as one or more additional computer systems 1021A, 1021B. Each computer system 1021A, 1021B can be configured similar to the computer system 1020, although a computer system 1021A, 1021B may not include a functional modeling interface 1030 and/or a distributed operating system 1032. As illustrated, each of the computer systems 1020, 1021A, 1021B may communicate with each other using any solution. When a functional model-based application 1036 is deployed to the computing environment 1010, the computer system 1020 may utilize one or more resources of another computer system 1021A, 1021B to execute the functional model-based application 1036. Such utilization can include providing at least a portion of the functional model-based application 1036 for execution on the computer system 1021A, 1021B (e.g., when the computer system 1021A, 1021B includes a distributed operating system 1032).

As described herein, some embodiments may address significant issues with respect to the design, development, and deployment of software applications. In particular, some embodiments can allow a user to design and deploy an application using a functional modeling solution, such that the application is not restricted to execution in any particular target computing environment. Additionally, some embodiments can address significant issued regarding the execution of applications in distributed computing environments. In particular, as the amount and/or types of resources available in these computing environments can be frequently changed, binding of the software application to a particular configuration of computing resources can be delayed until such binding is required during execution of the application.

Various Embodiments

While shown and described herein as a method and system for managing (e.g., designing, constructing, deploying, using, and modifying) software applications on a plurality of computing resources, which can operate collaboratively and in parallel, it is understood that various alternative or additional embodiments may be provided. For example, in various embodiments, a computer program is fixed in at least one computer-readable medium, which when executed, enables a computer system to manage software applications on a plurality of computing resources. To this extent, the computer-readable medium includes program code, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, a method provides a copy of program code, which enables a computer system to implement some or all of a process described herein. In this case, a computer system may process a copy of the program code to generate and transmit, for reception at a second, distinct location, a set of data signals that has one or more of its characteristics set and/or changed in such a manner as to encode a copy of the program code in the set of data signals. Similarly, some embodiments provide a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another example, a method provides generating a system for managing software applications on a plurality of computing resources. In this case, the generating may include configuring a computer system, such as the computer system 1020 (FIG. 10), to implement a method of managing software applications on a plurality of computing resources. The configuring may include obtaining (e.g., creating, maintaining, purchasing, modifying, using, making available, or the like) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The present invention(s) are described above with reference to example embodiments. It will be appreciated that various modifications may be made and other embodiments may be used without departing from the broader scope of the present invention(s). Therefore, these and other variations upon the example embodiments are intended to be covered by the present invention(s).

What is claimed is:

1. A system that dynamically determines desired functionality based on context of real-time events, constructs functional components based on the desired functionality, and executes the functional components in real-time on a deployment target as a contextually-motivated service, the system comprising:
    one or more processors; and
    memory storing instructions that, when executed by the one or more processors, cause the system to perform:
        detecting one or more real-time events and determining a context based on the one or more real-time events;
        fetching an application model based on the context and meta-data associated with the one or more real-time events, the application model referencing one or more micro-functions, each micro-function being a declarative model of one or more atomic functions and including at least one pre-condition descriptor and at least one post-condition descriptor;
        constructing a functional graph based on the one or more micro-functions of the application model;
        transforming the one or more micro-functions into a plurality of micro-capabilities, each micro-capability of the plurality of micro-capabilities being capable of satisfying at least one pre-condition of the at least one pre-condition descriptor and at least one post-condition of the at least one post-condition descriptor by:
            determining at least one computing resource for execution of at least one micro-capability of the plurality of micro-capabilities by matching pre-conditions of the at least one micro-capability of the plurality of micro-capabilities and matching post-conditions of the at least one micro-capability of the plurality of micro-capabilities;

enabling execution and configuration of the at least one micro-capability on the at least one computing resource by providing access in a target environment to an application program interface (API), the API capable of calling the at least one micro-capability to configure the at least one micro-capability on the at least one computing resource and execute the micro-capability on the at least one computing resource;

receiving a request to execute and configure the at least one micro-capability on the at least one computing resource from the target environment;

executing and configuring the at least one micro-capability on the at least one computing resource; and providing an output of the at least one micro-capability from the at least one computing resource to the target environment.

2. The system of claim 1, wherein the one or more real-time events include a real-time system request of the target environment.

3. The system of claim 2, wherein the real-time system request indicates an application object in a header of the real-time system request, and the context includes an identifier indicating the application object.

4. The system of claim 3, wherein the output of the at least one micro-capability from the at least one computing resource comprises a customized representation of the requested application object.

5. The system of claim 1, wherein the application model, the one or more micro-functions, the plurality of micro-capabilities, and the at least one computing resource are modeled from a root object defining base properties and capabilities.

6. The system of claim 1, further comprising a plurality of computing resources, wherein the plurality of computing resources includes the at least one computing resource, the plurality of computing resources providing a virtualized pool of resources, each of the plurality of computing resources being a virtualized infrastructure, a physical infrastructure, or a software-controlled device.

7. The system of claim 6, wherein the plurality of computing resources are distributed across a multi-dimensional network of nodes connected by one or more links.

8. The system of claim 1, wherein the at least one computing resource includes one or more computing resource descriptors, the one or more computing resource descriptors including an API descriptor associated with the API.

9. The system of claim 8, wherein the one or more computing resource descriptors comprise any of one or more local interfaces, local capabilities, local services, supporting services, and operating system kernels.

10. The system of claim 8, wherein the one or more computing resource descriptors facilitate management of thread handling, resources, and memory spaces for the at least one computing resource as an operating system performs for a singular virtual infrastructure unit, physical infrastructure unit, or software-controlled device.

11. A method that dynamically determines desired functionality based on context of real-time events, constructs functional components based on the desired functionality, and executes the functional components in real-time on a deployment target as a contextually-motivated service, the method comprising:

detecting one or more real-time events and determining a context based on the one or more real-time events;

fetching an application model based on the context and meta-data associated with the one or more real-time events, the application model referencing one or more micro-functions, each micro-function being a declarative model of one or more atomic functions and including at least one pre-condition descriptor and at least one post-condition descriptor;

constructing a functional graph based on the one or more micro-functions of the application model;

transforming the one or more micro-functions into a plurality of micro-capabilities, each micro-capability of the plurality of micro-capabilities being capable of satisfying at least one pre-condition of the at least one pre-condition descriptor and at least one post-condition of the at least one post-condition descriptor, by:

determining at least one computing resource for execution of at least one micro-capability of the plurality of micro-capabilities by matching pre-conditions of the at least one micro-capability of the plurality of micro-capabilities and matching post-conditions of the at least one micro-capability of the plurality of micro-capabilities;

enabling execution and configuration of the at least one micro-capability on the at least one computing resource by providing access in a target environment to an application program interface (API), the API capable of calling the at least one micro-capability to configure the at least one micro-capability on the at least one computing resource and execute the micro-capability on the at least one computing resource;

receiving a request to execute and configure the at least one micro-capability on the at least one computing resource from the target environment;

executing and configuring the at least one micro-capability on the at least one computing resource; and providing an output of the at least one micro-capability from the at least one computing resource to the target environment.

12. The method of claim 11, wherein the one or more real-time events include a real-time system request of the target environment.

13. The method of claim 12, wherein the real-time system request indicates an application object in a header of the real-time system request, and the context includes an identifier indicating the application object.

14. The method of claim 13, wherein the output of the at least one micro-capability from the at least one computing resource comprises a customized representation of the requested application object.

15. The method of claim 11, wherein the application model, the one or more micro-functions, the plurality of micro-capabilities, and the at least one computing resource are modeled from a root object defining base properties and capabilities.

16. The method of claim 11, further comprising determining a plurality of computing resources, wherein the plurality of computing resources includes the at least one computing resource, the plurality of computing resources providing a virtualized pool of resources, each of the plurality of computing resources being a virtualized infrastructure, a physical infrastructure, or a software-controlled device.

17. The method of claim 16, wherein the plurality of computing resources are distributed across a multi-dimensional network of nodes connected by one or more links.

18. The method of claim 11, wherein the at least one computing resource includes one or more computing resource descriptors, the one or more computing resource descriptors including an API descriptor associated with the API.

19. The method of claim 18, wherein the one or more computing resource descriptors comprise any of one or more local interfaces, local capabilities, local services, supporting services, and operating system kernels.

20. The method of claim 18, wherein the one or more computing resource descriptors facilitate management of thread handling, resources, and memory spaces for the at least one computing resource as an operating system performs for a singular virtual infrastructure unit, physical infrastructure unit, or software-controlled device.

21. A non-transitory computer readable medium comprising instructions that, when executed, cause one or more processors to perform:
 detecting one or more real-time events and determining a context based on the one or more real-time events;
 fetching an application model based on the context and meta-data associated with the one or more real-time events, the application model referencing one or more micro-functions, each micro-function being a declarative model of one or more atomic functions and including at least one pre-condition descriptor and at least one post-condition descriptor;
 constructing a functional graph based on the one or more micro-functions of the application model;
 transforming the one or more micro-functions into a plurality of micro-capabilities, each micro-capability of the plurality of micro-capabilities being capable of satisfying at least one pre-condition of the at least one pre-condition descriptor and at least one post-condition of the at least one post-condition descriptor, by:
  determining at least one computing resource for execution of at least one micro-capability of the plurality of micro-capabilities by matching pre-conditions of the at least one micro-capability of the plurality of micro-capabilities and matching post-conditions of the at least one micro-capability of the plurality of micro-capabilities;
  enabling execution and configuration of the at least one micro-capability on the at least one computing resource by providing access in a target environment to an application program interface (API), the API capable of calling the at least one micro-capability to configure the at least one micro-capability on the at least one computing resource and execute the micro-capability on the at least one computing resource;
 receiving a request to execute and configure the at least one micro-capability on the at least one computing resource from the target environment;
 executing and configuring the at least one micro-capability on the at least one computing resource; and
 providing an output of the at least one micro-capability from the at least one computing resource to the target environment.

* * * * *